US012653619B1

(12) United States Patent
Barhoush

(10) Patent No.: US 12,653,619 B1
(45) Date of Patent: Jun. 16, 2026

(54) MULTIMODAL SUBCUTANEOUS VASCULATURE VISUALIZATION AND AUGMENTED REALITY OVERLAYS FOR HANDS-FREE CLINICAL PROCEDURES

(71) Applicant: Plerion AI, Inc., San Diego, CA (US)

(72) Inventor: Amin Barhoush, San Diego, CA (US)

(73) Assignee: Plerion AI, Inc., San Diego, CA (US)

( * ) Notice: Subject to any disclaimer, the term of this patent is extended or adjusted under 35 U.S.C. 154(b) by 0 days.

(21) Appl. No.: 19/411,714

(22) Filed: Dec. 8, 2025

Related U.S. Application Data

(60) Provisional application No. 63/882,469, filed on Sep. 16, 2025.

(51) Int. Cl.
| | |
|---|---|
| *A61B 34/10* | (2016.01) |
| *A61B 34/20* | (2016.01) |
| *A61B 90/00* | (2016.01) |
| *A61B 90/50* | (2016.01) |
| *G06T 7/33* | (2017.01) |
| *G06T 7/50* | (2017.01) |

(Continued)

(52) U.S. Cl.
CPC .............. *A61B 34/10* (2016.02); *A61B 90/37* (2016.02); *G06T 7/344* (2017.01); *G06T 7/50* (2017.01); *G06T 19/006* (2013.01); *G06V 10/26* (2022.01); *A61B 2034/107* (2016.02); *A61B 2034/2065* (2016.02); *A61B 2090/365* (2016.02); *A61B 2090/366* (2016.02); *A61B 2090/502* (2016.02); *G06T 2207/10048* (2013.01); *G06T 2207/10081* (2013.01); *G06T 2207/10088* (2013.01); *G06T 2207/10101* (2013.01); *G06T 2207/10121* (2013.01); *G06T 2207/10132* (2013.01); *G06T 2207/30048* (2013.01); *G06T 2207/30101* (2013.01); *G06T 2207/30241* (2013.01); *G06T 2210/41* (2013.01); *G06V 2201/03* (2022.01); *G16H 30/20* (2018.01); *G16H 80/00* (2018.01)

(58) Field of Classification Search
None
See application file for complete search history.

(56) References Cited

U.S. PATENT DOCUMENTS

| | | | |
|---|---|---|---|
| 12,211,151 B1* | 1/2025 | Chiou | ................... G06T 19/003 |
| 2023/0157757 A1* | 5/2023 | Braido | ................... G16H 20/40 |
| | | | 345/419 |

(Continued)

*Primary Examiner* — James A Thompson
(74) *Attorney, Agent, or Firm* — FP; Sikander M. Khan

(57) ABSTRACT

A multimodal system, device, and method for capturing, processing, and overlaying subcutaneous vasculature and anatomical data onto extended reality (XR) displays, enabling hands-free visualization for clinical procedures. The system integrates one or more imaging modalities (e.g., ultrasound, near-infrared, infrared, photoacoustic imaging, optical coherence tomography, transillumination, hyperspectral imaging, laser speckle contrast) with AI-assisted processing pipelines to create real-time or pre-scanned overlays. The processed data is visualized via XR devices, including augmented reality (AR), mixed reality (MR), projection-based AR, and virtual reality (VR) systems. The system supports real-time segmentation, depth estimation, predictive analytics, adaptive overlays, and patient-specific recommendations, providing improved accuracy for vascular access, oncology, cardiology, neonatal care, trauma management, telemedicine, and other clinical workflows.

20 Claims, 26 Drawing Sheets

(51) Int. Cl.
    G06T 19/00           (2011.01)
    G06V 10/26           (2022.01)
    G16H 30/20           (2018.01)
    *G16H 80/00*           (2018.01)

(56)           References Cited

U.S. PATENT DOCUMENTS

| | | | |
|---|---|---|---|
| 2023/0404678 A1* | 12/2023 | Denissen | A61B 34/10 |
| 2024/0307122 A1* | 9/2024 | Tolkowsky | A61B 34/30 |
| 2024/0386682 A1* | 11/2024 | Cvetko | G06T 19/006 |
| 2026/0007484 A1* | 1/2026 | Brubaker | A61B 34/77 |

* cited by examiner

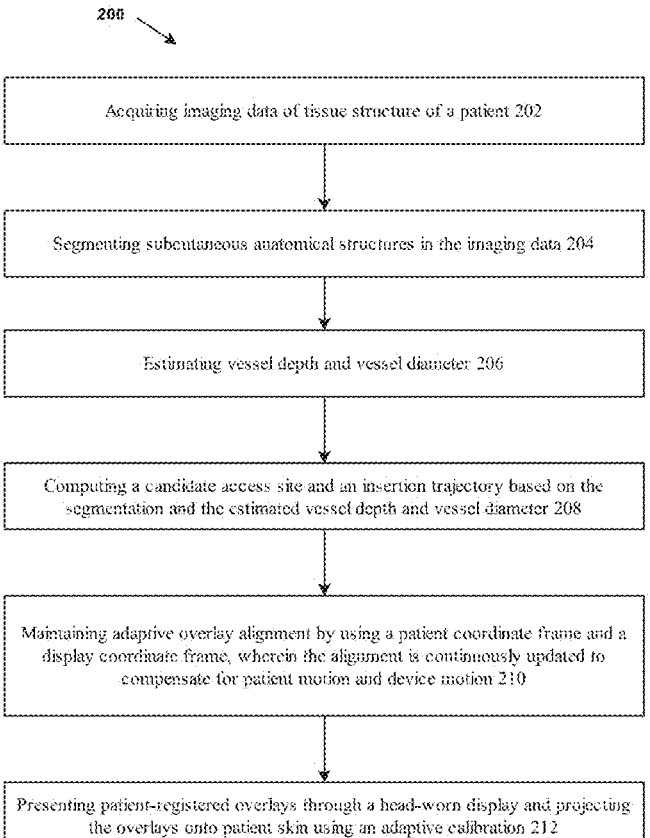

200

Acquiring imaging data of tissue structure of a patient 202

Segmenting subcutaneous anatomical structures in the imaging data 204

Estimating vessel depth and vessel diameter 206

Computing a candidate access site and an insertion trajectory based on the segmentation and the estimated vessel depth and vessel diameter 208

Maintaining adaptive overlay alignment by using a patient coordinate frame and a display coordinate frame, wherein the alignment is continuously updated to compensate for patient motion and device motion 210

Presenting patient-registered overlays through a head-worn display and projecting the overlays onto patient skin using an adaptive calibration 212

FIG. 2

OVERLAY IELEMTS 802
- Vein centerlines
- Diameter/depth labs 804
- Candidate site 806
- Trajectory arrow 808
- Safety band 810

Voice Prompt 814

Gaze Cursor 812

830

COMPOSITOR

PROJECTION
ON SKIN

828

832

PROJECTED
ON SKIN WITH
3D VIEW

838

826

OBSERVER VIEW

Merge to
patient frame

Inference Logic
1300

Inference Logic
1300

```
batch_size = tf.shape (x) [0]

x = self.rescale(x)

patches = self.extract_patches (x)

x = self.patch_proj (patches)

class_emb = tf.broadcast_to(
    self.class_emb, [batch_size, 1, self.d_model]
)

x = tf.concat([class_emb, x], axis=1)

x = x + self.pos_emb for layer in self.enc_layers:
    x = layer (x, training)

return  self.mlp_head(x[:, 0])
```

FIG. 22

MULTIMODAL SUBCUTANEOUS VASCULATURE VISUALIZATION AND AUGMENTED REALITY OVERLAYS FOR HANDS-FREE CLINICAL PROCEDURES

PRIORITY SECTION

This document is a United States Non-provisional utility patent application under statute 35 U.S.C. 111(A). This document claims priority and benefit to a U.S. Provisional utility patent application that is identified by a Serial No: 63/882,469 and that is titled "Multimodal Subcutaneous Vasculature Visualization and Augmented Reality Overlays for Hands-Free Clinical Procedures", and that was filed with the U.S. Patent and Trademark Office (USPTO) on Sep. 16, 2025. The above-referenced document is herein incorporated by reference in its entirety.

BACKGROUND OF TECHNOLOGY DISCLOSED

The "background" description provided herein is to generally present the context of the disclosure. Work of the presently named inventors, to the extent it is described in this background section, as well as aspects of the description which may not otherwise qualify as prior art at the time of filing, are neither expressly nor impliedly admitted as prior art against the present invention.

Modern healthcare workflows require clinicians to localize and access subsurface anatomical targets under diverse clinical conditions. Examples include peripheral and central vascular access, arterial line placement, blood sampling, targeted injections, and catheter-based interventions. Patient presentation varies widely across age, body habitus, hydration status, comorbidities, and movement, and clinical settings range from emergency departments and intensive care units to ambulatory clinics and home care. In these environments, systems are expected to capture and interpret heterogeneous signals, maintain spatial alignment with living tissue, and provide information in a format that does not interrupt sterile technique or procedural flow.

Several categories of guidance technologies exist. Optical vein visualization devices typically enhance superficial vasculature using narrow spectral bands and project a contrast-enhanced image on the skin or display it on a handheld screen. Ultrasound systems provide real-time cross-sectional views and Doppler flow information but are commonly operated on separate consoles that require manual probe handling and visual attention away from the procedure field. Tomographic or optical modalities such as optical coherence techniques, photoacoustic methods, hyperspectral imaging, and laser speckle contrast can reveal structural or perfusion-related information, yet they are often deployed as standalone instruments without unified spatial or temporal integration. Simulation and training platforms reproduce procedural scenarios but generally do not reflect live physiological variation or translate directly to bedside execution.

Existing solutions exhibit notable limitations. Many tools rely on a single sensing modality and lack mechanisms to combine complementary information across optical and acoustic domains. Display paradigms frequently separate the image from the physical site, requiring users to mentally map a two-dimensional screen to three-dimensional patient anatomy, which can increase cognitive load and error. Registration between sensed data and the patient is commonly transient or manual, and movement of the patient or operator can degrade alignment. Interaction is often controller-based or touch-driven, which may be impractical in sterile fields and for hands-busy procedures.

Broader informatics and operational challenges further constrain adoption. Guidance devices are commonly tethered to fixed consoles or networks and may not function reliably when connectivity is degraded. Model-based image processing, where present, is typically trained and updated in centralized repositories that require movement of sensitive data, creating privacy and governance concerns. Clinical documentation and audit trails are frequently decoupled from the guidance workflow, limiting traceability and quality improvement. Remote collaboration capabilities, when available, tend to overlay annotations on independent video feeds rather than on spatially registered patient views.

Persistent shortcomings can be identified across these approaches. Architectures are often modality-specific and do not support runtime selection or fusion of multiple imaging families within a single guidance pipeline. Spatial alignment is fragile, with limited support for motion compensation or sustained registration stability over the course of a procedure. Presentation modes are not consistently available in head-worn displays, projection onto patient surfaces, or other extended-reality paradigms, and interaction models may not be hands-free. Compute topologies are typically rigid, lacking graceful fallback between on-device, edge, and cloud execution. Finally, privacy-preserving mechanisms that enable learning from local outcomes without exporting raw patient data are not widely integrated.

Accordingly, there exists a need for systems and methods that unify multimodal capture of subsurface anatomical information, process such information to derive procedure-relevant spatial representations and metrics, maintain robust registration to living tissue under motion, and present guidance in forms suited to clinical practice. Such systems should support hands-free interaction, operate across variable compute and network conditions, interoperate with clinical records and audit workflows, enable remote collaboration with spatially meaningful annotations, and incorporate privacy-preserving learning to improve performance over time. These capabilities are necessary to enhance accuracy, reduce procedural attempts and complications, and improve efficiency and safety across a range of clinical environments.

SUMMARY OF INVENTION

A In an exemplary embodiment, a system comprises an imaging system configured to acquire imaging data of tissue structure and anatomical structures of a patient. The system further comprises processing circuitry comprising at least one processor and memory storing instructions that, when executed by the at least one processor, cause the processing circuitry to: segment anatomical structures in the imaging data; estimate a target depth and a target dimension for a target anatomical structure; compute a candidate access site and a trajectory comprising at least one of an insertion path and an incision path based on the segmentation and the estimated target depth and the estimated target dimension; and maintain adaptive overlay alignment by using a patient coordinate frame and a display coordinate frame, wherein the alignment is continuously updated to compensate for patient motion and device motion. The system further comprises an extended-reality device, comprising a head-worn display and a projection module, configured to present patient-registered overlays through the head-worn display and to project the overlays onto patient skin using an adaptive calibration.

In another exemplary embodiment, a computer-implemented method comprises acquiring imaging data of tissue structure and anatomical structures of a patient; segmenting anatomical structures in the imaging data; estimating a target depth and a target dimension for a target anatomical structure; computing a candidate access site and a trajectory comprising at least one of an insertion path and an incision path based on the segmentation and the estimated target depth and the estimated target dimension; maintaining adaptive overlay alignment by using a patient coordinate frame and a display coordinate frame, wherein the alignment is continuously updated to compensate for patient motion and device motion; and presenting patient-registered overlays through a head-worn display and projecting the overlays onto patient skin using an adaptive calibration.

In another exemplary embodiment, a non-transitory computer-readable storage medium stores instructions that, when executed by one or more processors of a system comprising a capture subsystem, a processing subsystem, and an extended-reality rendering subsystem, cause the system to perform: acquiring imaging data of tissue structure and anatomical structures of a patient; segmenting anatomical structures in the imaging data; estimating a target depth and a target dimension for a target anatomical structure; computing a candidate access site and a trajectory comprising at least one of an insertion path and an incision path based on the segmentation and the estimated target depth and the estimated target dimension; maintaining adaptive overlay alignment by using a patient coordinate frame and a display coordinate frame, wherein the alignment is continuously updated to compensate for patient motion and device motion; and presenting patient-registered overlays through a head-worn display and projecting the overlays onto patient skin using an adaptive calibration.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIG. 2 is a flow diagram illustrating an example computer-implemented method 200 for image-guided visualization and assistance, according to certain embodiments.

FIG. 22 shows example software code that implements a Transformer block.

DETAILED DESCRIPTION

Figure 1A:
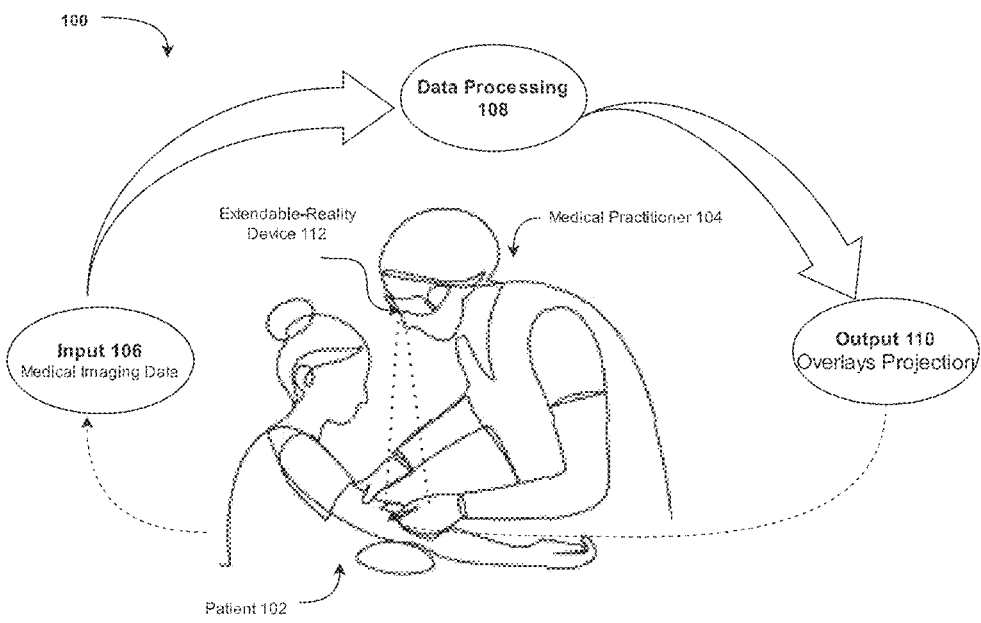
FIG. 1A is a schematic diagram illustrating an example system for image-guided visualization and assistance, according to certain embodiments.

The following description generally presents the context of the disclosure and elaborates example embodiments that support the claimed subject matter. The logical boundaries and data flows described herein are illustrative and non-limiting; individual modules may be combined, subdivided, or distributed across wearable devices, bedside workstations, mobile devices, and cloud services without departing from the described operation. Unless otherwise stated, examples are non-exclusive and terminology follows the usage in the claims and supporting materials.

Aspects of this disclosure are directed to computer-implemented systems and methods that deliver patient-registered visual guidance for subcutaneous access and related procedures through an extended-reality (XR) interface. Conventional practice is hindered by poor visualization of subcutaneous vessels across diverse phenotypes, operator-dependent interpretation of single-modality images, unstable guidance under patient and device motion, fragmented workflows across imaging, planning, and documentation systems, limited capability for hands-free interaction in sterile environments, insufficient mechanisms to encode institution-approved safety constraints, and inadequate support for remote collaboration and privacy-preserving model improvement. These shortcomings contribute to misalignment between images and anatomy, suboptimal site selection, elevated attempt counts, inconsistent documentation, and diminished training transferability.

The disclosed solution provides an integrated capture-processing-XR rendering platform. An imaging system acquires imaging data of tissue structure using one or more modalities (e.g., ultrasound, infrared/near-infrared, photoacoustic, optical coherence tomography, transillumination, hyperspectral, laser speckle; optionally CT/MRI/X-ray). Processing circuitry segments subcutaneous anatomical structures, estimates vessel depth and vessel diameter, and computes a candidate access site and an insertion trajectory under institution-approved constraints that include at least a minimum vessel-diameter threshold, a maximum insertion-depth threshold, and exclusion buffers around identified arteries. Registration maintains adaptive overlay alignment by continuously estimating a transform between a patient coordinate frame and a display coordinate frame via sensor fusion of depth/structured-light/LiDAR, inertial measurements, and acoustic or ultrasound beacons; projection calibration is derived from a three-dimensional surface model and is automatically refreshed when an alignment-confidence metric falls below a threshold. An extended-reality device, comprising a head-worn display and a projection module, presents patient-registered overlays and projects entry markers, direction vectors, depth gauges, safety bands, and mixed-reality reconstructions onto patient skin. A hands-free interaction module supports voice, gesture, gaze, and haptic inputs to confirm a candidate access site, adjust overlay parameters, change capture configuration, capture audit snapshots, and consult guidelines. Clinical interfaces log procedure records, retrieve or store data in an EHR/PACS, and provide an observer view and a telemedicine path for remote annotations that are merged into the overlays in real time. Federated learning module clients update segmentation and stabilization models using site-local signals without transmitting raw patient data, with staged rollout and rollback controls. Deployments span on-device runtimes with offline fallback, edge nodes, and cloud services.

By unifying multimodal acquisition, discrimination of arteries and veins, metric estimation, policy-constrained planning, motion-robust registration, XR presentation, hands-free control, clinical interoperability, telepresence, and privacy-preserving model lifecycle management, the invention remedies the identified deficiencies. It improves first-attempt success likelihood (via predictive indicators encoded in the overlays), reduces misalignment-induced error through adaptive calibration and confidence-gated presentation, enforces institution-approved safety profiles, streamlines documentation and training, enables remote expert participation, and maintains data stewardship while continuously improving performance across sites.

Environment

FIG. 1A is a schematic diagram illustrating an example system 100 for image-guided visualization and assistance in accordance with embodiments of the present disclosure. As discussed herein, system 100 includes logic, circuitry, and program instructions that enable the operations described in this specification when executed. In one embodiment, system 100 may be characterized as an apparatus including means for acquiring medical imaging data, means for processing the data, and means for presenting patient-registered visual overlays to a medical practitioner. In various embodiments, portions of the functionality of system 100 execute on one or more computing devices local to the point of care, on an edge workstation, on a cloud compute service, or on any combination thereof.

The system 100 includes a patient 102 and a medical practitioner 104 situated in a clinical setting. The practitioner 104 is depicted wearing an extendable-reality device 112 (also referred to as an XR device), which enables hands-free visualization and interaction. The XR device 112 may be implemented as a head-worn display (e.g., smart glasses with optical see-through or video pass-through), a mixed-reality headset, a virtual-reality headset used in pass-through mode, or a projection unit configured to project graphics onto the patient's skin. The XR device 112 includes display optics and/or a projection module, one or more processors, inertial sensors, one or more cameras, depth or structured-light sensors, microphones for voice input, and network interfaces for wired or wireless communication. In some embodiments, XR device 112 further provides gaze tracking, gesture sensing, and haptic output to facilitate hands-free operation by practitioner 104.

The system 100 further includes an input 106 representing medical imaging data associated with patient 102. Input 106 encompasses live or stored signals originating from one or more imaging modalities, including by way of example ultrasound, infrared (IR) or near-infrared (NIR) imaging, photoacoustic imaging, optical coherence tomography (OCT), transillumination, hyperspectral imaging, and laser speckle contrast imaging. In certain embodiments, input 106 also encompasses radiologic sources such as computed tomography (CT), magnetic resonance imaging (MRI), and X-ray or fluoroscopic imaging retrieved from local devices or from institutional archives. Input 106 may be provided by probes or scanners operated by practitioner 104, by sensors integrated into XR device 112, or by external systems connected over a wired or wireless network.

Data processing 108 denotes processing circuitry configured to receive input 106 and to generate patient-registered visual output for presentation via XR device 112. Data processing 108 includes one or more processors (e.g., CPUs, GPUs, or neural accelerators), system memory storing program instructions and intermediate data, and optionally local persistent storage. In one embodiment, data processing 108 executes a pipeline comprising preprocessing of imaging data, segmentation of subcutaneous anatomical structures (e.g., veins, arteries, anatomical landmarks), computation of vessel-related metrics (e.g., depth and diameter), and generation of access-planning information (e.g., candidate insertion site and insertion trajectory). In another embodiment, data processing 108 executes a registration engine configured to maintain a transform between a coordinate frame attached to patient 102 and a coordinate frame attached to XR device 112, and to continuously update that transform to compensate for patient and device motion. In further embodiments, data processing 108 includes an overlay compositor configured to synthesize graphical elements (e.g., vessel centerlines, depth/diameter labels, trajectory arrows, and safety bands) for delivery to XR device 112.

Output 110 represents the visualization presented to practitioner 104 as patient-registered overlays or as projected graphics on the patient's skin. In embodiments using a head-worn display, output 110 comprises an augmented view in which the computed overlays are rendered in alignment with the underlying anatomy visible to practitioner 104. In embodiments using a projection unit, output 110 comprises a projected pattern aligned to the three-dimensional surface of patient 102. Output 110 may further include user-interface elements suitable for hands-free operation, such as a gaze cursor, voice prompts, and context-appropriate status indicators that reflect alignment confidence, safety thresholds, or system state. In some configurations, output 110 is simultaneously mirrored to an observer display for training or remote consultation.

The elements of system 100 are operatively coupled to form a data flow. Medical imaging data at input 106 is transmitted to data processing 108 over a wired or wireless link. Data processing 108 computes the overlays and alignment parameters and transmits the resulting visualization to output 110 for presentation via XR device 112 to practitioner 104. Feedback signals, such as device pose measurements, gaze vectors, confirmation actions, or calibration prompts, are provided from XR device 112 back to data processing 108 to enable adaptive stabilization and interaction. In implementations that incorporate historical imaging, data processing 108 may retrieve prior studies, register them to the current patient coordinate frame maintained at runtime, and incorporate the registered information into the visualization delivered by output 110.

In one embodiment, the entirety of data processing 108 resides on XR device 112, thereby providing an on-device configuration suitable for low-connectivity environments. In another embodiment, preprocessing and segmentation execute on a nearby edge workstation while registration and overlay compositing execute on XR device 112. In yet another embodiment, model training and validation occur on a cloud service while only validated models are deployed to the point of care; the runtime path from input 106 to output 110 remains local and latency-optimized. These and other deployment configurations provide flexibility across clinical settings while preserving the functional relationships illustrated in FIG. 1A.

System Architecture

Figure 1B:
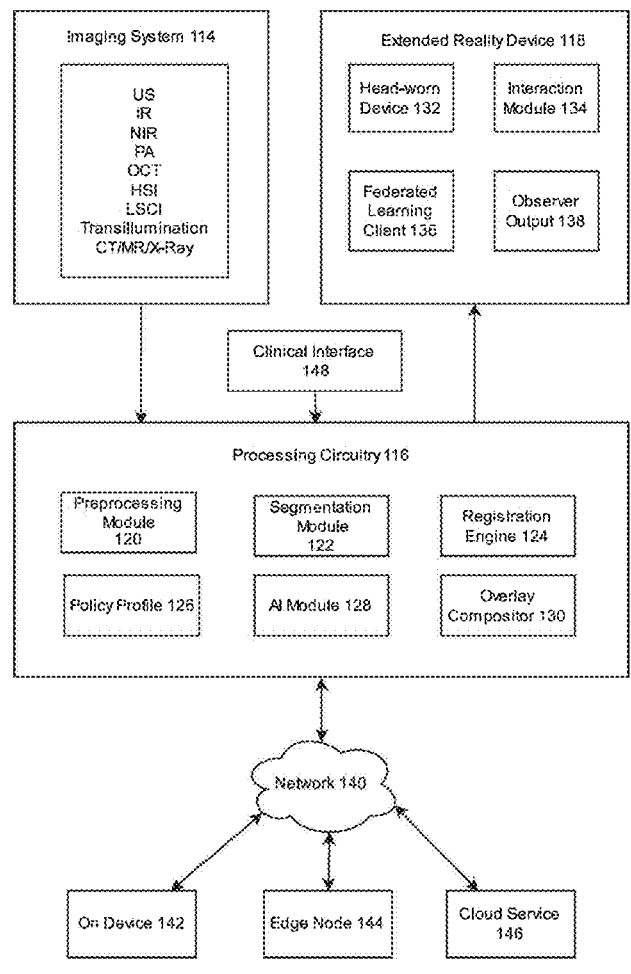
FIG. 1B is a block diagram illustrating a system for multimodal capture, processing, and extended-reality visualization, according to certain embodiments.

FIG. 1B is a block diagram illustrating an example system 100 for multimodal capture, processing, and extended-reality visualization, in accordance with embodiments of the present disclosure. System 100 includes an imaging system 114, processing circuitry 116, an extended-reality device 118, a clinical interface, and a network 140 that communicatively couples the processing circuitry 116 to an on-device tier 142, an edge node 144, and a cloud service 146. The elements of FIG. 1B are arranged to acquire imaging data of tissue structure of a patient, to segment subcutaneous anatomical structures in the imaging data, to estimate vessel depth and vessel diameter, to compute a candidate access site and an insertion trajectory based on the segmentation and the estimated vessel depth and vessel diameter, to maintain adaptive overlay alignment by using a patient coordinate frame and a display coordinate frame, and to present patient-registered overlays through a head-worn display and to project the overlays onto patient skin using an adaptive calibration. In addition, the same architecture acquires and processes imaging data describing other anatomical structures and materials beyond vessels and arteries, including but not limited to organs, soft tissues, nerves, tendons, musculoskeletal elements, tumours, lesions, calculi, and foreign bodies such as shrapnel or bullets; segments such anatomical structures; estimates depths, dimensions, shapes, and margins of such anatomical structures; and computes incision or insertion sites and trajectories suitable for tissue biopsy, drain placement, foreign-body localization, and echocardiography guidance using stored or live imaging, while preserving the adaptive overlay alignment and presentation behaviors described herein.

The imaging system 114 is a capture subsystem configured to acquire imaging data of tissue structure of a patient using one or more imaging modalities. In the illustrated embodiment, the imaging system 114 supports ultrasound (US), infrared (IR), near-infrared (NIR), photoacoustic imaging (PA), optical coherence tomography (OCT), transillumination, hyperspectral imaging (HSI), and laser speckle contrast imaging (LSCI). In another embodiment, the imaging system 114 further interfaces with computed tomography (CT), magnetic resonance imaging (MRI), and X-ray or fluoroscopic imaging. The imaging system 114 may include handheld probes, cart-based scanners, wearable sensors, or room-mounted instruments that provide live streams, and may also accept stored imaging objects retrieved via the clinical interface. The imaging system 114 outputs raw or preprocessed frames and associated metadata (for example, probe pose, intrinsic parameters, and time-stamps) to the processing circuitry 116. These modalities enable additional use cases in which the same capture pathway acquires echocardiography views for cardiac overlays, CT/MRI-derived three-dimensional organ or tumor reconstructions for registration on the body surface, and optical sequences for detection of surgical landmarks and foreign bodies prior to or during intervention.

The processing circuitry 116 is a compute subsystem comprising at least one processor and memory storing instructions that, when executed by the at least one processor, implement the operations described herein. In various embodiments, the at least one processor includes one or more central processing units (CPUs), graphics processing units (GPUs), tensor or neural processing units (NPUs), digital signal processors (DSPs), field-programmable gate arrays (FPGAs), application-specific integrated circuits (ASICs), or any combination thereof. The memory includes volatile memory (for example, DRAM) and non-volatile memory (for example, flash, solid-state drives, or persistent memory). The processing circuitry 116 executes a modular pipeline that includes a preprocessing module 120, a segmentation module 122, a registration engine 124, a policy profile 126, an AI module 128, and an overlay compositor 130. The same pipeline is configurable to operate on vessel-centric studies as well as non-vascular anatomies such as nerves and tendons for regional anesthesia planning, organ targets for image-guided biopsy, and embedded foreign bodies for surgical retrieval.

The preprocessing module 120 is configured to normalize and condition input data for downstream analysis. In one embodiment, the preprocessing module 120 performs operations such as speckle reduction and time-gain compensation for ultrasound, spectral unmixing for hyperspectral imaging and photoacoustic imaging, intensity normalization for infrared and near-infrared frames, and geometry rectification for structured-light or LiDAR depth maps. The preprocessing module 120 aligns modality timestamps and generates harmonized frames suitable for multimodal processing.

When CT, MRI, or fluoroscopy are available, the preprocessing module 120 also performs volume resampling, intensity standardization, and surface extraction so that organ contours, tumor margins, and bony landmarks are available to subsequent modules.

The segmentation module 122 is configured to segment subcutaneous anatomical structures in the imaging data. In one embodiment, the segmentation module 122 generates vein masks, artery masks, vessel centerlines, and anatomical landmarks. In another embodiment, model-based segmentation utilizes prior imaging volumes as anatomical priors or patient-specific digital-twin references to improve overlay stability and predictive accuracy during repeat procedures. The segmentation outputs are provided to the AI module 128 for measurement and planning. Extended embodiments further segment nerves, tendons, muscle planes, organ boundaries, cardiac chambers and valves, masses, and foreign bodies; produce centerlines or surface meshes for such segmented targets; and emit label confidences for downstream planning and visualization.

The AI module 128 is configured to estimate vessel depth and vessel diameter and to compute a candidate access site and an insertion trajectory based on the segmentation and the estimated vessel depth and vessel diameter. In one embodiment, the AI module 128 evaluates constraints comprising at least a minimum vessel-diameter threshold, a maximum insertion depth, and an exclusion buffer around an identified artery. The constraints are loaded from the policy profile 126. In another embodiment, the AI module 128 computes a predictive indicator of procedural success for the candidate access site using historical outcome data and encodes the predictive indicator for display within overlays. In a further embodiment, the processing circuitry 116 references prior procedural records to identify previously used or contraindicated insertion sites and automatically suppresses candidate access sites or trajectories in the identified regions. The same AI module 128 generalizes these computations to non-vascular targets by estimating target depth, target extent, safe approach corridors relative to segmented critical structures (for example, nerves or arteries), and recommended incision or insertion trajectories for biopsy or foreign-body retrieval; it also provides a selectable overlay-only mode in which the system renders patient-registered information without generating automated recommendations, allowing the clinician to choose a site and depth manually while preserving guidance for alignment and safety.

The registration engine 124 is configured to maintain adaptive overlay alignment by using a patient coordinate frame and a display coordinate frame, wherein the alignment is continuously updated to compensate for patient motion and device motion. In one embodiment, the registration is based on sensor fusion of signals from at least two sensor types selected from depth sensing, structured light, LiDAR, inertial measurement, and acoustic or ultrasound beacons. For projection, the processing circuitry 116 derives a projection calibration from a three-dimensional patient surface model and updates the projection calibration responsive to motion. When an alignment confidence metric drops below a preset value, overlay presentation is inhibited or a recalibration prompt is projected. In another embodiment, infrared or green-light reflectance frames are co-registered to the patient coordinate frame and used to generate a projected safety mask that excludes regions with poor superficial venous contrast. These same registration and calibration routines support organ-level overlays for echocardiography and CT/MRI-derived models, enabling accurate alignment of cardiac structures, abdominal organs, or tumor volumes in mixed- or augmented-reality views.

The policy profile 126 is a data structure and enforcement module configured to provide institution-approved parameters and procedural thresholds to the processing pipeline. In one embodiment, the policy profile 126 supplies the minimum vessel-diameter threshold, the maximum insertion depth, and the artery exclusion buffer used by the AI module 128. In another embodiment, the policy profile 126 stores alignment confidence thresholds, documentation requirements, and presentation parameters, and logs applied constraints with a procedure record. Profiles also encode organ- or procedure-specific constraints such as nerve-sparing corridors, maximum biopsy needle angles, exclusion margins around previously placed devices, and recency-based suppression that avoids puncturing the same skin area within a configured look-back interval.

The overlay compositor 130 is configured to generate patient-registered overlays for presentation to a user. In one embodiment, the overlay compositor 130 renders vein centerlines, diameter and depth labels, candidate access sites, insertion trajectories, safety bands, and predictive indicators. In another embodiment, the overlay compositor 130 produces mixed-reality synthetic three-dimensional reconstructions of subcutaneous anatomical structures. The overlay compositor 130 outputs synchronized streams suitable for a head-worn display and, when present, for a projection module. Additional compositions include overlays of organ contours and tumor volumes from prior CT/MRI registered to current surface geometry, echocardiography target windows for acoustic windows selection, projected search grids for foreign-body localization, and overlays that switch between recommendation mode and overlay-only mode under user control.

The clinical interface is a bidirectional integration interface configured to store and retrieve clinical information. In one embodiment, the clinical interface retrieves historical imaging data from a picture-archiving and communication system and from an electronic health record, and the processing circuitry 116 registers the historical imaging data with real-time imaging for longitudinal visualization. In another embodiment, the clinical interface logs a procedure record including the candidate access site, the insertion trajectory, the imaging modalities used, and presentation parameters, and stores the procedure record in an electronic health record. In a further embodiment, the extended-reality device 118 or an associated camera captures an image of an insertion or incision site, associates the image with spatial coordinates, timestamps, and operator identifiers, and uploads an annotated record to the electronic health record via the clinical interface. For broader anatomical workflows, the clinical interface also retrieves prior biopsy targets, operative notes describing retained foreign bodies, and cardiac measurements, and it writes structured summaries of target selection, approach parameters, and compliance with local policy profiles.

The extended-reality device 118 is a presentation and interaction subsystem configured to deliver patient-registered visualization and hands-free control. In one embodiment, the extended-reality device 118 comprises a head-worn display 132 and an interaction module 134. The head-worn display 132 is configured to present patient-registered overlays in pass-through or mixed-reality modes. In another embodiment, the extended-reality device 118 further includes a projection module configured to project the overlays onto patient skin using the adaptive calibration maintained by the registration engine 124. The interaction module 134 provides a hands-free interaction module offering voice commands, gesture recognition, gaze selection, and haptic input. The processing circuitry 116 accepts a user action to confirm a candidate access site, adjust overlay parameters, or change a capture configuration. The extended-reality device 118 further includes a federated learning module 136, alternatively referred to as a federated learning client 136, and an observer output 138. The federated learning client 136 is configured to update model parameters by a federated learning procedure using site-local training signals without transmitting raw patient imaging data outside a deployment site, and to receive validated models from the cloud service 146 with staged rollout and rollback hooks. The observer output 138 is configured to present, to an external display, a synchronized view of the patient-registered overlays and to accept a remote expert input that is incorporated into the overlays. In one embodiment, a telemedicine interface receives remote annotations and merges the remote annotations into the patient-registered overlays in real time by encoding patient-frame coordinates and applying the merge within the overlay compositor 130. These presentation and interaction features extend to organ overlays for echocardiography training and guidance, to tumor targeting during percutaneous biopsy, and to search-path visualization for foreign-body retrieval.

The network 140 is a communication fabric configured to carry messages, frames, and model artifacts between components of system 100. In various embodiments, the network 140 includes one or more of Ethernet, Wi-Fi, cellular network (i.e., 5G, 6G or any such upcoming technologies), Bluetooth Low Energy, and wired serial links. The network 140 couples the processing circuitry 116 to the on-device tier 142, the edge node 144, and the cloud service 146 to support multiple deployment topologies.

In a first deployment embodiment, on-device, the processing circuitry 116 executes on an on-device tier (e.g., a wearable head-worn display or a co-located portable unit). The on-device tier is configured to perform the segmenting of subcutaneous anatomical structures, the estimating of vessel depth and vessel diameter, the computing of the candidate access site and the insertion trajectory, the maintaining of adaptive overlay alignment using a patient coordinate frame and a display coordinate frame, and the presenting of patient-registered overlays. This embodiment supports an offline fallback mode in which procedure guidance proceeds without network connectivity and, upon restoration of connectivity, synchronizes procedure metadata and model updates. The same on-device configuration supports overlays for nerves, tendons, organs, tumors, and foreign bodies when bandwidth or privacy constraints require local inference.

In a second deployment embodiment, edge-assisted configuration, latency-sensitive stages including registration, overlay compositing, and hands-free interaction, execute on the on-device tier, while an edge node performs multimodal fusion of imaging data, analytics, archival, observer-view encoding, or retrieval of historical imaging data from a picture-archiving and communication system or an electronic health record. The edge node is configured to cache models and study assets, to reduce round-trip latency, and to return fused, patient-registered overlays to the on-device tier for presentation. This embodiment enables richer cardiac and organ reconstructions, tumor-tracking analytics, and foreign-body search accelerators without impacting interactive latency.

In a cloud-assisted configuration, the cloud service 146 provides model training, a model registry, and secure aggregation for federated learning; the runtime path for latency-sensitive rendering remains on the on-device tier 142 and the edge node 144. The processing circuitry 116 is configured to operate in an offline fallback mode and to synchronize procedure metadata when connectivity is restored. Cloud-trained models may include generalized biopsy-planning policies, cross-modality registration networks for CT/MRI to surface alignment, and models that support overlay-only mode or recommendation mode based on institutional preference.

In yet another in a fourth deployment embodiment, the system dynamically selects among the on-device tier, the edge node, and the cloud service based on measured latency, bandwidth, and compute availability. If the alignment confidence metric or connectivity drops below a threshold, the system inhibits overlay presentation or projects a recalibration prompt and transitions to a reduced-dependency mode that preserves the maintaining of adaptive overlay alignment and the presenting of overlays using locally available models and policies. The same selection logic applies to vascular and non-vascular scenarios alike, including echocardiography training sessions, percutaneous biopsy planning, and foreign-body localization.

The foregoing deployment embodiments are non-limiting. Variations may partition the preprocessing, segmentation, registration, policy enforcement, trajectory computation, overlay compositing, clinical interface operations, telemedicine relay, and documentation capture across one or more devices or services according to clinical, regulatory, privacy, and performance requirements. The system is not limited to the aforementioned implementations.

Figure 1C:
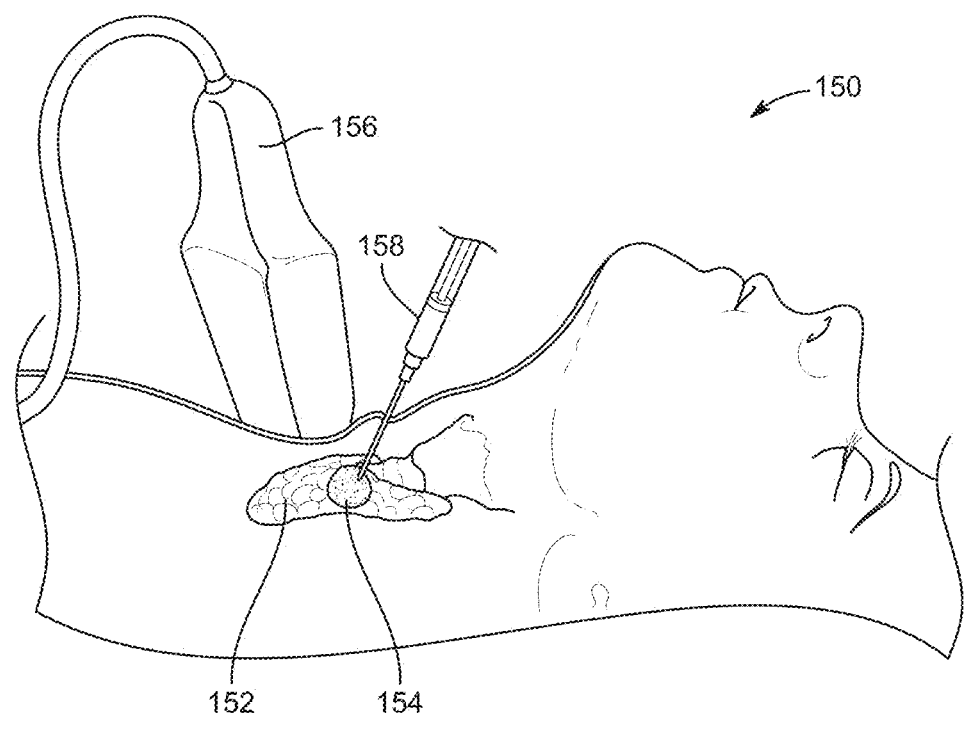
FIG. 1C is an exemplary illustration of an anatomical guidance overlay for a medical imaging device 1 imaging a thyroid with a thyroid nodule, according to certain embodiments.

FIG. 1C is an exemplary illustration of an anatomical guidance overlay generated by the system for a medical imaging device 156, according to certain embodiments. In the illustrated example, the medical imaging device 156 comprises an ultrasound probe positioned over a patient's neck to acquire a live image of a thyroid 152. A thyroid nodule 154 is depicted as a target lesion within the thyroid 152. A composite overlay is registered to the live image and delineates not only veins, arteries, and other blood vessels in the imaging plane, but also additional anatomical structures, including soft-tissue compartments, organs such as the thyroid 152, bones, cartilage, ligaments, tendons, peripheral nerves, pathologic masses such as the thyroid nodule 154, and non-biologic foreign bodies. For each depicted structure, the system estimates depth, local diameter or cross-sectional size, and spatial relationships to surrounding tissues using the same artificial-intelligence processing chain that estimates vessel depth and vessel diameter. In one implementation, the same artificial-intelligence processing chain estimates a depth and size of parenchymal tissues and lesions to guide interventional radiology procedures, such as needle biopsy of the thyroid nodule 154 or other lesions under ultrasound, computed tomography, X-ray, fluoroscopy, or other imaging modalities registered to the overlay. In another implementation, the composite overlay incorporates foreign bodies localized from real-time imaging or registered historical imaging (for example, a bullet or other retained object) so that a surgeon can use the overlay to plan a retrieval path through overlying tissue. For cardiac applications, the composite overlay may represent a three-dimensional cardiac structure derived from prior echocardiography, computed tomography, or X-ray imaging and registered to a current echocardiographic view so that a technician can move the transducer to appropriate intercostal windows while observing the overlay of the heart. Based on these estimates, a trajectory planner computes one or more candidate insertion or incision paths from the skin surface to a selected target, and determines for each path an associated insertion site, insertion angle, and insertion depth that respect clearance margins from critical structures. The candidate access sites and trajectories are rendered as graphical overlays on the live ultrasound image from the medical imaging device 156, together with numeric indicators of depth or path length, thereby enabling a clinician to select a vein for cannulation, a lesion such as the thyroid nodule 154 for biopsy, a foreign body for retrieval, or another anatomical target while the overlay remains registered in real time as the medical imaging device 156 is repositioned.

Figure 1D:
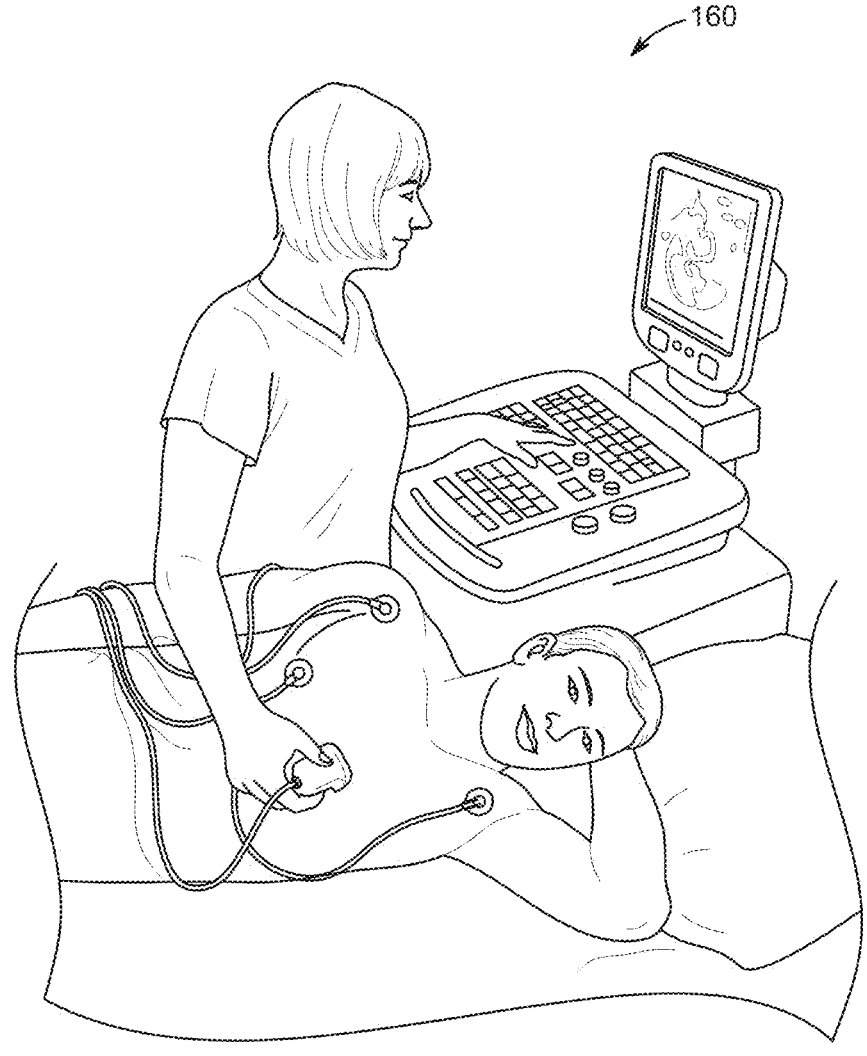
FIG. 1D is an exemplary illustration of a user interface presenting clinician-controlled anatomical overlays and AI-generated guidance options, according to certain embodiments.

FIG. 1D is an exemplary illustration of a user-interface workflow for clinician-controlled anatomical guidance using the overlay of FIG. 1C, according to certain embodiments. The overall image 160 depicts the same composite overlay of vascular and non-vascular anatomy, including veins, arteries, organs, nerves, tendons, tumors, foreign bodies, and cardiac structures, superimposed on a current or previously acquired medical image. A control panel within the overall image 160 provides user-selectable controls that permit a clinician to toggle an AI recommender mode on or off. In an overlay-only mode, the system continues to segment and classify anatomical structures and to display their depth and spatial extent as an anatomical map within the overall image 160 but suppresses automatic insertion-site and trajectory recommendations so that the clinician may rely solely on the overlay to decide where and how deep to insert an instrument. In a recommender-enabled mode, the overall image 160 presents suggested insertion sites, trajectories, and depths computed by the AI planner, and allows the clinician to accept, adjust, or reject each suggestion via the user interface for venous access, lesion biopsy, foreign-body retrieval, physiotherapy guidance, or cardiac imaging guidance.

In one embodiment, the overall image 160 further illustrates historical access information rendered on the overlay as markers corresponding to recent insertions or punctures, together with exclusion zones derived from a procedure log. The system records the time, location, and depth of previous access events, uses historical data of very recent insertions to identify insertion sites in the same site, and automatically avoids proposing new candidate insertion sites within a configurable spatiotemporal proximity of those events, thereby reducing repeated puncture of the same skin or vessel segment within a short time interval. In this particular embodiment, the processing circuitry records, for each insertion or incision event, a procedure log entry comprising at least a spatial location of the insertion or incision site on the patient, an associated trajectory and depth, a timestamp, and one or more operator identifiers. The processing circuitry stores the procedure log in association with the patient record and defines, for each recorded event, a corresponding exclusion region within a configurable spatial neighborhood of the recorded site and a configurable temporal window following the event. When the system subsequently computes candidate access sites and trajectories for a new procedure, the processing circuitry references the historical procedural data, identifies previously used or contraindicated access locations within the temporal window, and automatically suppresses or deprioritizes candidate access sites and trajectories whose spatial locations fall within the exclusion regions. In this manner, the system uses historical data of very recent insertions to avoid insertion sites in the same site and reduces repeated puncture of the same skin area or vessel segment within a short time proximity.

In yet another example, a control panel within the overall image 160 provides user-selectable controls that permit a clinician to toggle an AI recommender mode on or off. In an overlay-only mode, the system continues to segment and classify anatomical structures and to display their depth and spatial extent as an anatomical map within the overall image 160, but suppresses automatic insertion-site and trajectory recommendations so that the clinician may rely solely on the overlay to decide where and how deep to insert an instrument.

Method

FIG. 2 is a flow diagram illustrating an example computer-implemented method 200 for image-guided visualization and assistance, in accordance with embodiments of the present disclosure. The operations of method 200 are performed by one or more processors of processing circuitry executing instructions stored in memory and interacting with an imaging system and an extended-reality device.

At step 202, the method includes acquiring imaging data of tissue structure of a patient. In various embodiments, the acquiring includes receiving live image streams from one or more modalities such as ultrasound, infrared, near-infrared, photoacoustic imaging, optical coherence tomography, transillumination, hyperspectral imaging, and laser speckle contrast imaging, and in certain embodiments further includes computed tomography, magnetic resonance imaging, and X-ray or fluoroscopic imaging. In some embodiments, the acquiring includes retrieving historical imaging data from a picture-archiving and communication system or an electronic health record and time-synchronizing, calibrating, and normalizing the imaging data for downstream processing.

At step 204, the method includes segmenting subcutaneous anatomical structures in the imaging data. In one embodiment, the segmenting generates vein masks, artery masks, vessel centerlines, and anatomical landmarks suitable for measurement and planning. In another embodiment, model-based segmentation utilizes prior imaging volumes as anatomical priors or patient-specific digital-twin references to improve stability across frames and repeat procedures.

At step 206, the method includes estimating vessel depth and vessel diameter. In one embodiment, the vessel depth is computed relative to a three-dimensional surface model of patient skin and the vessel diameter is computed from segmented lumen width along a centerline; the estimating may produce confidence or uncertainty values for each measurement.

At step 208, the method includes computing a candidate access site and an insertion trajectory based on the segmentation and the estimated vessel depth and vessel diameter. In one embodiment, the computing evaluates constraints comprising at least a minimum vessel-diameter threshold, a maximum insertion depth, and an exclusion buffer around an identified artery, and selects an entry point, a direction vector, and a target depth that satisfy the constraints. In another embodiment, the computing includes determining a predictive indicator of procedural success for the candidate access site using historical outcome data and encoding the predictive indicator for presentation.

At step 210, the method includes maintaining adaptive overlay alignment by using a patient coordinate frame and a display coordinate frame, wherein the alignment is continuously updated to compensate for patient motion and device motion. In one embodiment, the maintaining includes sensor fusion of signals from at least two sensor types selected from depth sensing, structured light, LiDAR, inertial measurement, and acoustic or ultrasound beacons to estimate transforms between the coordinate frames. In projection embodiments, a projection calibration is derived from the three-dimensional surface model and is updated responsive to motion; when an alignment confidence metric drops below a preset value, overlay presentation is inhibited or a recalibration prompt is projected.

At step 212, the method includes presenting patient-registered overlays through a head-worn display and projecting the overlays onto patient skin using an adaptive calibration. In various embodiments, the overlays comprise vein centerlines, diameter and depth labels, a candidate access site, an insertion trajectory, safety bands, and optional predictive indicators. The presenting may include rendering an observer view on an external display and, in telemedicine embodiments, receiving and merging remote annotations encoded in patient-frame coordinates in real time.

Multimodal Input Capture

Figure 3:
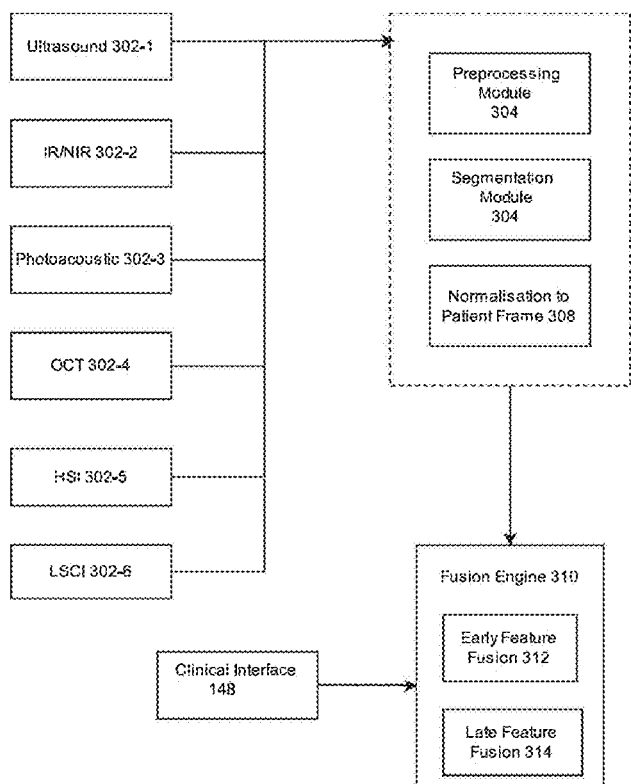
FIG. 3 is a block diagram illustrating a multimodal capture and fusion pipeline, according to certain embodiments.

FIG. 3 is a block diagram illustrating a multimodal capture and fusion pipeline, in accordance with embodiments of the present disclosure. The pipeline of FIG. 3 receives imaging data from a plurality of modality sources, 302-1 through 302-6, performs preprocessing 304 and segmentation 306, normalizes outputs to a patient coordinate frame at 308, and combines live and historical information in a fusion engine 310 having an early feature fusion stage 312 and a late feature fusion stage 314. A clinical interface 316 supplies prior studies and procedure context for longitudinal visualization and model priors. The fused outputs are provided to downstream stages of the processing platform that estimate vessel depth and vessel diameter, compute a candidate access site and an insertion trajectory based on the segmentation and the estimated vessel depth and vessel diameter, and generate patient-registered overlays for extended-reality presentation.

The multi-modality sources, 302-1 through 302-6, constitute an imaging intake configured to acquire imaging data of anatomical structure of a patient using one or more imaging modalities. The anatomical structure may include, but may not be limited to, includes at least one of vessels, organs, nerves, tendons, musculoskeletal structures, pathological masses, and foreign bodies. In the illustrated embodiment, source 302-1 denotes ultrasound, which may include B-mode, color Doppler, and spectral Doppler channels provided by handheld or cart-based transducer arrays with wired or wireless links. Source 302-2 denotes infrared and near-infrared reflectance imaging using eye-safe emitters and band-pass filtering for superficial venous contrast. Source 302-3 denotes photoacoustic imaging in which pulsed optical excitation generates ultrasonic responses captured by a detector array, yielding oxygenation-sensitive maps. Source 302-4 denotes optical coherence tomography providing micrometer-scale cross-sections of superficial structures. Source 302-5 denotes hyperspectral imaging in which each pixel carries a spectrum suitable for deriving oxygen saturation and tissue composition indices. Source 302-6 denotes laser speckle contrast imaging that measures flow-related speckle dynamics for superficial perfusion. The intake supports real-time streaming for live guidance and batch ingestion for review, training, and simulation. In certain configurations, multiple modality sources operate concurrently, with synchronized timestamps and calibration metadata, to provide complementary contrast mechanisms suitable for segmentation, discrimination of veins and arteries, and quantification of vessel geometry. Device interfaces include universal serial bus, Ethernet, and local wireless transports such as Wi-Fi or Bluetooth Low Energy. Time synchronization can be provided by clock discipline on the host or precision time protocol when supported.

Preprocessing 304, according to an embodiments, adapts each incoming stream to a normalized representation for analysis. For ultrasound, preprocessing 304 may perform time-gain compensation, dynamic-range compression, speckle reduction, and temporal compounding. For IR or near-infrared frames, preprocessing 304 may perform illumination normalization, vignetting correction, and contrast enhancement. For hyperspectral and photoacoustic frames, preprocessing 304 may perform spectral calibration, wavelength registration, and spectral unmixing to produce oxygenation or absorber-specific images. For optical coherence tomography, preprocessing 304 may perform dewarping, dispersion compensation, and frame alignment. For laser speckle contrast imaging, preprocessing 304 may compute speckle contrast maps over configurable exposure windows and convert them to relative flow indices. Across modalities, preprocessing 304 may remove sensor artifacts, stabilize handheld motion, and resample to a common spatial grid with consistent pixel spacing and orientation. The outputs of preprocessing 304 include modality-normalized frames and feature volumes with timestamps and intrinsic or extrinsic calibration tags.

The segmentation module 306 performs automated delineation and labeling of anatomical structures and objects across supported imaging modalities. The segmentation module 306 ingests modality-normalized frames and produces per-structure masks, edges, centerlines, landmarks, and instance labels with associated confidences in the range 0.0-1.0. The segmentation module 306 operates on soft-tissue compartments, organs, bony cortex, cartilage, ligaments, tendons, skeletal muscle groups, peripheral nerves, skin and fascial planes, pathologic masses including tumors and cystic lesions, and non-biologic objects including implanted hardware and foreign bodies. The segmentation module 306 accepts ultrasound, Doppler, infrared, near-infrared, hyperspectral, photoacoustic, optical coherence tomography, laser speckle contrast, structured-light depth, LiDAR, X-ray or fluoroscopic, CT, and MRI inputs, and the segmentation module 306 registers prior volumes to live frames when available so that the segmentation module 306 uses anatomical priors or patient-specific digital-twin references to stabilize labels across repeat sessions.

The segmentation module 306 employs classical vessel-ness, contour, and morphology operators together with learned encoder-decoder networks and transformer-based architectures to generate pixel- and voxel-level labels. The segmentation module 306 fuses information from multiple modalities by concatenating encoder features for early fusion, and by combining modality-specific confidence maps for late fusion, so that geometric cues, texture cues, spectral absorption cues, and motion cues reinforce one another. The segmentation module 306 attaches a confidence score to each pixel, voxel, centerline node, or object instance and forwards the confidences to downstream metric estimation, trajectory computation, and overlay presentation so that a full-opacity overlay is rendered in high-confidence regions, a dim overlay is rendered in moderate-confidence regions, and an operator confirmation is prompted in low-confidence regions.

In a vascular-guidance embodiment, the segmentation module 306 generates a vein mask, an artery mask, vessel centerlines, and anatomical landmarks. The segmentation module 306 distinguishes arteries from veins by integrating modality-specific signatures and temporal behavior. Spectral and color Doppler reveal pulsatile arterial flow distinct from venous phasic or steady flow; photoacoustic and hyperspectral inputs yield wavelength-dependent absorption and oxygen-saturation maps that indicate higher oxygenation for arterial structures; morphological cues such as wall thickness, circularity, depth relative to the skin surface, and compressibility under gentle ultrasound pressure provide further separation; and frame-to-frame variance detects heartbeat-synchronized diameter changes characteristic of arteries. When two or more modalities are active, the segmentation module 306 combines features as described with reference to early feature fusion stage 312 and late decision fusion to improve classification robustness. The segmentation module 306 assigns a confidence score in the 0.0-1.0 range to each vascular label and propagates the scores to access-planning stages.

In an interventional-oncology or interventional-radiology embodiment, the segmentation module 306 delineates a target lesion in liver, lung, kidney, or soft tissue, segments adjacent critical structures including bile ducts, pleura, and neurovascular bundles, and emits a composite label map that a downstream planner uses to recommend a safe skin entry, a three-dimensional direction vector, and a target depth that avoid critical anatomy while honoring policy constraints. In a foreign-body-localization embodiment, the segmentation module 306 identifies a metallic fragment on ultrasound or X-ray, segments neighboring tendons, nerves, and vessels, and provides a centerline approach path for overlay presentation; by way of illustration, the segmentation module 306 can segment a retained bullet within the forearm, label the median nerve and radial artery as no-go zones, and output an approach corridor that preserves a minimum clearance while indicating depth to the bullet along the planned trajectory. In a cardiology embodiment, the segmentation module 306 registers a prior cardiac model or cine loop and segments chambers, valves, and great vessels in real time so that an extended-reality renderer overlays guidance for standardized acoustic windows during echocardiography. In a rehabilitation embodiment, the segmentation module 306 segments joint surfaces, tendons, and muscle groups and outputs bony and soft-tissue landmarks that anchor joint-angle gauges and range-of-motion visualizations.

These embodiments renders vascular capability while generalizing the segmentation module 306 to a comprehensive anatomical and object-segmentation engine that supports biopsy guidance, foreign-body retrieval, cardiac imaging assistance, and musculoskeletal therapy within the same pipeline and with confidence-aware outputs that maintain antecedent linkage to subsequent measurement, trajectory, and overlay components.

Normalization module 308 is configured to register the outputs of segmentation module 306 to a patient coordinate frame. In one embodiment, normalization module 308 uses extrinsic transforms derived from depth sensing, structured light, LiDAR, inertial measurement, or acoustic or ultrasound beacons to map images, masks, and centerlines into a common patient-anchored space. Normalization may also align historical studies that are retrieved through the clinical interface 316 and provide surface-to-volume mappings when prior volumetric data such as computed tomography or magnetic resonance reconstructions are available. The result is a set of modality-agnostic layers that are spatially consistent across time, modalities, and viewpoints, enabling downstream estimation of vessel depth from the skin surface model and estimation of vessel diameter from cross-sectional measurements along the normalized centerlines.

The fusion engine 310 is configured to combine information across modalities and time to generate a unified vessel representation with associated metrics and confidence attributes. The fusion engine 310 includes an early feature fusion stage 312 and a late feature fusion stage 314. Early feature fusion stage 312 is performed on intermediate feature volumes aligned by normalization and aggregates complementary features such as Doppler-derived pulsatility, oxygenation indices, and ultrasound texture descriptors into a composite feature tensor. The composite tensor is supplied to segmentation 306 in a recurrent or iterative manner to refine boundaries, labels, and centerlines under challenging conditions including low signal-to-noise ratio, edema, or motion. Late feature fusion 314 operates on modality-specific decisions and confidence maps returned by segmentation 306. Late feature fusion 314 reconciles per-modality masks and centerlines using learned or rule-based weighting that accounts for modality confidence, field-of-view differences, and latency, thereby producing a consensus vessel map and consolidated confidence scores. When historical data are present, late feature fusion 314 integrates aligned priors to stabilize labels across repeat sessions. The fused outputs provide inputs for estimation of vessel depth and vessel diameter and for computation of a candidate access site and an insertion trajectory based on the segmentation and the estimated vessel depth and vessel diameter in subsequent stages of the processing platform.

In one embodiment, the clinical interface 316 retrieves historical imaging data, radiology reconstructions, or reports from a picture-archiving and communication system or an electronic health record and provides the retrieved data to normalization for alignment to the current patient coordinate frame and to the fusion engine 310 for inclusion in early feature fusion 312 or late feature fusion 314. In another embodiment, the clinical interface 316 supplies prior procedural records and expert annotations that can be interpreted as constraints or labels for artery or vein classification and can inform planning stages that suppress candidate access sites or trajectories in previously used or contraindicated regions. Data transfer through the clinical interface 316 can be performed over secure, authenticated channels and may include de-identification in accordance with institutional privacy policy.

In operation, live frames from modality sources 302-1 through 302-6 are received by preprocessing 304, segmented by segmentation 306, normalized by normalization to the patient coordinate frame, and combined by the fusion engine 310. When made available by the clinical interface 316, historical imaging is aligned and fused alongside live data. The resulting unified representation includes vein and artery labels, centerlines, landmarks, and confidence attributes sufficient for downstream estimation of vessel depth and vessel diameter, computation of a candidate access site and an insertion trajectory, and generation of patient-registered overlays for presentation on a head-worn display and projection onto patient skin using an adaptive calibration. The ordering and partitioning shown in FIG. 3 are illustrative. In alternate embodiments, early feature fusion 312 precedes the first pass of segmentation 306 for all modalities, late feature fusion 314 reconciles periodic updates from each modality at different frame rates, or both stages operate concurrently to balance accuracy and latency across on-device, edge, and cloud deployments.

Artery and Vein Classification

Figure 4:
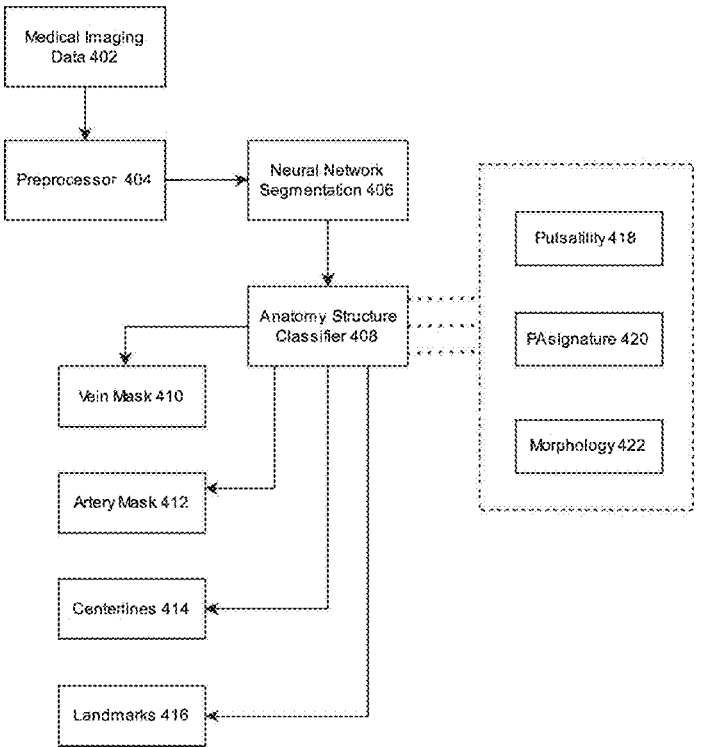
FIG. 4 is a block diagram illustrating a segmentation and artery-vein classification subsystem, according to certain embodiments.

FIG. 4 is a block diagram illustrating a segmentation and classification subsystem 400, in accordance with embodiments of the present disclosure. The subsystem 400 refines the processing chain introduced in FIG. 1B by detailing how medical imaging data are conditioned, segmented, and classified to yield outputs suitable for metric estimation and overlay generation. The subsystem 400 includes medical imaging data 402, a preprocessor 404, a neural-network segmentation module 406, an Anatomy Structure Classifier 408, alternatively referred to as a classifier 408, and output artifacts comprising a vein mask 410, an artery mask 412, vessel centerlines 414, and anatomical landmarks 416, with internal feature families including a pulsatility feature set 418, a photoacoustic/optical absorption feature set 420, and a morphology feature set 422.

The anatomical landmark 416 denotes a machine-readable reference entity produced by the segmentation module 306 and classifier 408. The processing circuitry assigns each anatomical landmark 416 a type identifier, a geometric representation, a confidence value, and coordinates in the patient coordinate frame maintained by the registration engine 124. The geometric representation may be a point (e.g., bifurcation apex, bone protuberance), a curve or centerline segment (e.g., tendon course, nerve fascicle path), a surface patch (e.g., cortical bone plate, cartilage facet), or a volumetric ROI (e.g., lymph node, soft-tissue mass, foreign body). The system stores per-landmark attributes including normal vectors, local curvature, scale, temporal stability, and appearance descriptors that link the anatomical landmark 416 back to contributing modalities and timestamps.

Medical imaging data 402 denotes frames or volumes acquired by the imaging system of FIG. 1B using one or more modalities described therein. The medical imaging data 402 are supplied to the preprocessor 404. The preprocessor 404 adapts modality-specific characteristics to a normalized representation. Examples include time-gain compensation, dynamic-range compression, speckle reduction, and temporal compounding for ultrasound; illumination normalization and contrast enhancement for infrared and near-infrared; spectral calibration, wavelength registration, and spectral unmixing for hyperspectral and photoacoustic sequences to obtain oxygenation-related maps; dewarping, dispersion compensation, and frame alignment for optical coherence tomography; and speckle-contrast computation for laser speckle contrast imaging. The preprocessor 404 outputs modality-normalized frames with timestamps and calibration tags.

The neural-network segmentation module 406 receives the normalized frames from the preprocessor 404 and segments subcutaneous anatomical structures in the imaging data. The neural-network segmentation module 406 implements a multi-stage approach that includes classical filters, learned models, temporal modeling, and probabilistic weighting so that motion-robust visual guidance is maintained across supported modalities. Classical components include multiscale Frangi or Sato vesselness filters that highlight tubular structures using image-Hessian eigenvalues; active-contour or Chan-Vese level-set algorithms that refine vessel-wall boundaries based on edge gradients and region homogeneity; and morphological operators with connected-component analysis and skeletonization to extract centerlines and bifurcation points. Learned components include convolutional networks such as U-Net or Attention U-Net for pixel-level classification of veins, arteries, and surrounding tissues, and transformer-based or hybrid ConvNeXt-Transformer models that incorporate long-range spatial context for diffuse contrast or poor ultrasound signal quality. When two or more modalities are present, the neural-network segmentation module 406 supports early fusion by concatenating encoder features across modalities and late fusion by combining modality-specific confidence maps using Bayesian or weighted averaging. Temporal stability may be provided by ConvLSTM or 3D-CNN units that process sequential frames to suppress flicker during patient or operator motion. Training for the neural-network segmentation module 406 uses annotated datasets that combine synthetic, simulated, and de-identified clinical frames with expert labels for lumen boundaries, wall positions, and centerlines. Typical training patch sizes are 256×256 or 512×512 pixels; learning rates are between $1\times10^{-4}$ and $5\times10^{-4}$ with Adam or RMSProp optimizers; model sizes range from 1 to 25 million parameters to enable edge-optimized and cloud inference modes; and data augmentation includes spatial rotation up to ±15 degrees, intensity scaling, and elastic deformation.

The classifier 408 receives outputs of the neural-network segmentation module 406 together with engineered features and assigns artery or vein labels with confidence values by integrating Doppler-derived pulsatility, optical absorption profiles, morphological and temporal characteristics, and learned multimodal classifiers, with ground-truth references established during model training and adaptive refinement through clinical feedback. In acoustic modalities, arteries exhibit pulsatile flow patterns synchronized with the cardiac cycle, whereas venous flow is phasic or steady and may vary with respiration; spectral Doppler analysis identifies high-velocity triphasic or biphasic arterial flow profiles contrasted with low-velocity monophasic venous waveforms, and temporal and frequency-domain features are extracted from Doppler channels to classify vessel type. In photoacoustic imaging, wavelength-dependent contrast based on hemoglobin oxygenation provides separation; oxygenated hemoglobin concentration is typically higher in arterial blood, producing distinct spectral absorption ratios that label vessels as arterial or venous. In near-infrared or hyperspectral imaging, an oxygen saturation index (an $SpO_2$ map) separates arteries, which generally present higher oxygenation, from veins, which generally present lower oxygenation. Morphological and spatial cues are exploited: arteries tend to have thicker walls, rounder cross-sections, and deeper subcutaneous depth compared to veins, which are more compressible and tortuous; when ultrasound or structured-light depth data are available, wall stiffness under gentle probe pressure or compression response is used as a differentiator. Temporal dynamics and motion coupling are further considered: arteries demonstrate periodic diameter expansion synchronized to the heartbeat, and frame-to-frame analysis or temporal-variance filters detect pulsatile motion patterns that are absent or minimal in venous structures.

When multiple modalities are active, the classifier 408 performs feature-level fusion that combines the pulsatility feature set 418, the photoacoustic/optical absorption feature set 420, and the morphology feature set 422 into a composite classifier. A trained neural network or a probabilistic rule engine assigns a confidence score to each label (artery, vein, or uncertain) and propagates these confidences into downstream access planning. During model training and calibration, ground-truth labels for arteries and veins are established through manual expert annotation of ultrasound cine loops, correlation with invasive catheter placements, or reference imaging such as CT angiography and MR angiography in de-identified datasets. Confidence metrics, expressed as 0-1 probability scores, are encoded in the segmentation mask and visualized in extended-reality overlays to indicate classification certainty. In deployment, classification may be refined adaptively from user confirmation (for example, a clinician marking a vessel as venous or arterial during access) or from real-time feedback such as pulsatile backflow detection; these signals are incorporated into federated model updates so that discrimination accuracy improves over time without transmitting raw patient data outside the site.

The classifier 408 outputs the vein mask 410, the artery mask 412, the vessel centerlines 414, and the anatomical landmarks 416 together with confidence values computed as described above. Overlay stabilization operates in concert with the neural-network segmentation module 406 and the classifier 408. Inter-frame motion vectors are estimated using optical-flow methods such as Lucas-Kanade or RAFT and are filtered by Kalman or extended-Kalman filters to smooth trajectory updates and reject outliers when inertial or depth signals are present elsewhere in the system. During stabilization, confidence-weighted blending preserves visual continuity while preventing misleading guidance in low-confidence regions. For real-time deployment, the neural-network segmentation module 406 and the classifier 408 are quantized for execution on embedded GPUs or NPUs of a head-worn device or an edge node so that frame-to-overlay latency remains below 100 milliseconds; model versions and calibration states are logged with the procedure record for audit.

In operation, the medical imaging data 402 are conditioned by the preprocessor 404, segmented by the neural-network segmentation module 406, and labeled by the classifier 408 to produce the vein mask 410, the artery mask 412, the vessel centerlines 414, and the anatomical landmarks 416 with confidences. These outputs are consumed by the processing circuitry of FIG. 1B to estimate vessel depth and vessel diameter, to compute a candidate access site and an insertion trajectory based on the segmentation and the estimated vessel depth and vessel diameter, and to maintain adaptive overlay alignment for patient-registered presentation.

The present embodiment is not limited to artery and vein classification. The classifier 408 also classifies soft-tissue compartments, organs, bones, cartilage, ligaments, tendons, peripheral nerves, pathologic masses, and non-biologic objects including implanted hardware and foreign bodies, with corresponding confidence values that drive incision planning, avoidance-zone overlays, documentation, and extended-reality presentation.

Trajectory Computation

Figure 5:
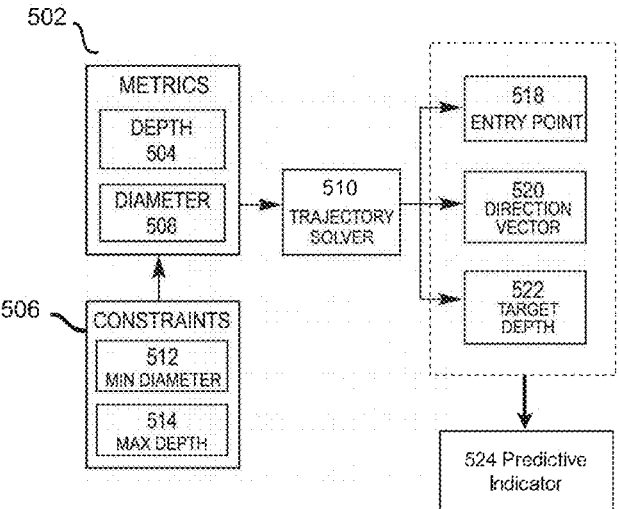
FIG. 5 illustrates exemplary use case workflows in pharmacy automation, hospital care, and executive productivity, according to certain embodiments.

FIG. 5 is a block diagram illustrating a metrics and trajectory computation subsystem 500, in accordance with embodiments of the present disclosure. The subsystem 500 consumes outputs produced by the segmentation and classification pipeline of FIG. 4 and generates access-planning parameters that are rendered as patient-registered overlays by the extended-reality device of FIG. 1B. It is to be noted that, though the below embodiments described in conjunction with FIG. 5 to FIG. 12 relate to arteries and vessel, the present disclosure is not limited to segmentation and classification of arteries and vessels, rather, it relates to segmentation and classification of other anatomical structures, such as organs, tissues and so on, and foreign bodies inside the patient's body, such as a bullet, as well.

A metrics block 502 receives vessel masks, centerlines, and landmarks and is configured to estimate vessel depth and vessel diameter for one or more segmented vessels. A depth estimator 504 measures a perpendicular distance from a three-dimensional surface model of patient skin to a corresponding vessel centerline. A diameter estimator 508 derives a wall-to-wall distance for the same vessel, for example from ultrasound cross-sections or from optical contrast models when acoustic measurements are not available. The metrics block 502 outputs depth and diameter values together with per-measurement confidence scores that indicate statistical reliability. Confidence values are represented as normalized probabilities in the range of 0.0 to 1.0, where values above 0.8 indicate high reliability, values between 0.5 and 0.8 indicate moderate confidence, and values below 0.5 indicate low confidence that may trigger re-acquisition or user confirmation. For peripheral veins, diameters are approximately 1.5 mm to 6 mm and access depths are approximately 1 mm to 15 mm below the skin surface. For deeper vessels such as central or femoral veins, diameters are approximately 6 mm to 20 mm with depths extending to approximately 30 mm or greater depending on patient anatomy and body habitus. Arteries, where visualized for exclusion or reference, may exhibit diameters between approximately 2 mm and 10 mm at superficial sites. These numerical values are illustrative and non-limiting. The system adapts to detected vessel scale using dynamic normalization factors derived from depth sensing and imaging resolution.

A constraints block 506 provides planning limits that are applied during trajectory computation. The constraints block 506 may be populated from an institution-approved practice-guideline profile (e.g., INS Infusion Therapy Standards, ASA Central Venous Access Guidelines, NICE TA49, AVA Vessel Health & Preservation, ACEP ultrasound guidance) or from operator input and, in the embodiment shown, includes a minimum access diameter 512 and a maximum insertion depth 514. In one configuration, the minimum access diameter 512 is at least 2 mm and the maximum insertion depth 514 is at most 25 mm so that safe procedure planning is maintained. The policy-based profiles parameterize additional rules including a maximum target depth as a function of catheter length and insertion angle, exclusion buffers around arteries identified in the segmentation, a maximum number of attempts, and site-selection rules; profiles may be selected per institution and per procedure and are auditable for quality improvement. Additional criteria considered by the constraints block 506 include distance to bifurcations, local vessel tortuosity, tissue path, and device reachability. Where enabled, the constraints block 506 also accepts in-procedure Human-in-the-Middle feedback to refine future presets.

A trajectory solver 510 receives the vessel depth and vessel diameter from the metrics block 502 with associated confidences and enforces the constraints from the constraints block 506. The trajectory solver 510 is configured to compute a candidate access site and an insertion trajectory based on the segmentation and the estimated vessel depth and vessel diameter. In one embodiment, the trajectory solver 510 minimizes a cost function defined in Equation [TRAJ-1] subject to inequality constraints defined in Equation [SAFE-1]. The cost function may penalize excessive insertion depth, steep approach angles, and paths that pass near an artery identified by the classification subsystem, while honoring profile-specified exclusion buffers and attempt limits. The optimization yields a set of geometric parameters comprising an entry point 518 on the patient surface, a direction vector 520 indicating the approach orientation, and a target depth 522 indicating the intended depth along the direction vector. The trajectory solver 510 continuously updates these parameters so that changes in measured depth, measured diameter, registration quality, or motion state are reflected in real time.

A predictive indicator 524 receives the entry point 518, the direction vector 520, the target depth 522, and the confidences associated with the underlying measurements and is configured to compute a predictive indicator of procedural success for the candidate access site. The predictive indicator 524 may be generated from historical outcome data together with vessel geometry, approach angle, and constraint satisfaction to produce a probability or score as described in Equation [RISK-1]. The resulting score is encoded within the overlays so that an operator is provided with a clear, patient-registered visualization of the entry point, the direction vector, and the target depth together with the associated likelihood of success. Confidence values are propagated to the predictive indicator 524 and to the overlays so that regions with lower reliability are dimmed or annotated accordingly.

In operation, the subsystem 500 estimates vessel depth and vessel diameter at the metrics block 502, applies safety limits at the constraints block 506, computes the candidate access site and the insertion trajectory at the trajectory solver 510, and produces the entry point 518, the direction vector 520, and the target depth 522. The predictive indicator 524 encodes a probability of success or risk level for the candidate plan. These parameters are forwarded to the registration and overlay compositor described in FIG. 1B; the registration uses the patient coordinate frame and the display coordinate frame to maintain adaptive overlay alignment and, responsive to motion, updates projection calibration and overlay state as described with motion-compensation behavior in FIGS. 7A-7C.

Access Planning

Figure 6:
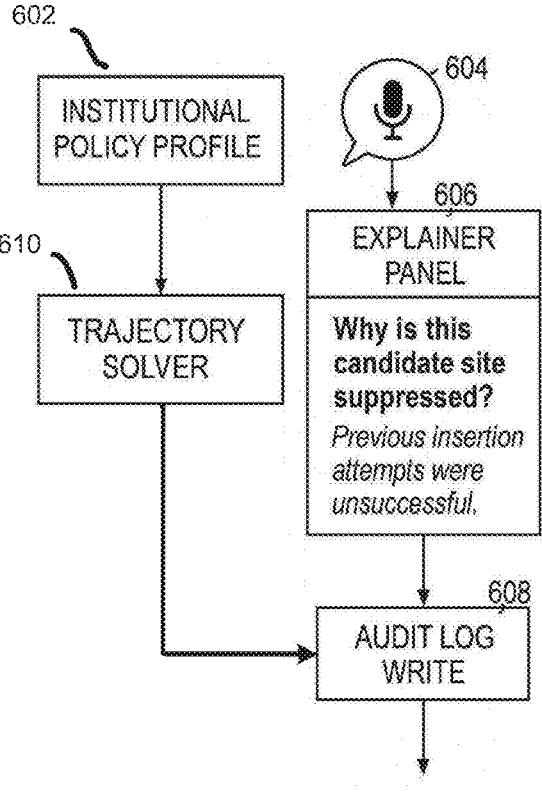
FIG. 6 is a block diagram illustrating a policy-driven access-planning subsystem, according to certain embodiments.

FIG. 6 is a block diagram illustrating a policy-driven access-planning subsystem 600, in accordance with embodiments of the present disclosure. The subsystem 600 refines the access-planning workflow introduced in FIG. 1B by showing how a trajectory solver within the processing circuitry ingests an institutional policy profile, how a hands-free "consult guidelines" interaction is handled, and how explanatory and audit outputs are generated.

An institutional policy profile 602 denotes a machine-readable bundle of practice parameters that is configured to constrain access planning. The institutional policy profile 602 may be retrieved from an external practice-guideline source or from a clinical information system and may be versioned. In one embodiment, the institutional policy profile 602 parameterizes at least: a minimum vessel-diameter threshold, a maximum insertion depth as a function of catheter length and insertion angle, an exclusion buffer around an artery identified in the segmentation, a maximum number of attempts, and site-selection rules. Profiles may be selected per institution and per procedure and are auditable for quality improvement. Illustratively and without limitation, the minimum vessel-diameter threshold may be at least 2 mm and the maximum insertion depth may be at most 25 mm for peripheral venous access, although other values may be specified by the institutional policy profile 602. The institutional policy profile 602 is further configured to be logged with a profile name and a version identifier so that overlays display whether a current recommendation conforms to an active guideline profile.

A trajectory solver 610 is a component of the processing circuitry and is configured to compute a candidate access site and an insertion trajectory based on the segmentation and the estimated vessel depth and vessel diameter while enforcing the constraints specified by the institutional policy profile 602. The insertion trajectory may be defined by a skin entry point, a three-dimensional direction vector, and a target depth to a vessel centerline with safety margins. The trajectory solver 610 enforces constraints to avoid an artery identified in the segmentation and to satisfy at least the minimum vessel-diameter threshold and the maximum insertion-depth threshold. Additional criteria implemented by the trajectory solver 610 may consider distance to bifurcations, local vessel tortuosity, tissue path, and device reachability. Where enabled, the trajectory solver 610 may compute a predictive indicator of procedural success from historical outcome data and encode the predictive indicator within patient-registered overlays.

A hands-free interaction input 604 represents a user invocation of a "consult guidelines" command as part of a hands-free interaction module. The hands-free interaction input 604 may be received as a voice command through a head-worn device or a companion wearable. In operation, the hands-free interaction input 604 triggers retrieval of context-specific recommendations from the institutional policy profile 602, for example an ultrasound-first recommendation for an internal jugular central venous catheter procedure, and queries the trajectory solver 610 for any constraints that have caused a candidate access site or an insertion trajectory to be suppressed.

An explainer panel 606 is configured to render, within the extended-reality device or an associated display, a textual and graphical explanation that cites the applicable portions of the institutional policy profile 602 and the specific constraint evaluations performed by the trajectory solver 610. By way of illustration, the explainer panel 606 may present a message indicating that a candidate site is suppressed because previous insertion attempts were unsuccessful, because the minimum vessel-diameter threshold was not satisfied, or because an exclusion buffer around an identified artery would be violated. The explainer panel 606 may also present indicators of conformance to the active guideline profile.

An audit log write 608 is configured to persist, to a procedure record or to an electronic health record through the clinical interface described in FIG. 1B, the candidate access site, the insertion trajectory, the imaging modalities used, presentation parameters, timestamps, operator identifiers, device metadata, the profile name and version of the institutional policy profile 602, the result of the constraint evaluation performed by the trajectory solver 610, and any user interaction including the hands-free "consult guidelines" invocation.

In operation, the institutional policy profile 602 supplies constraint presets to the trajectory solver 610, the hands-free interaction input 604 initiates context-specific consultation, the explainer panel 606 surfaces the reasons for acceptance or suppression of a candidate plan, and the audit log write 608 commits the resulting artifacts to a clinical record. This policy-driven loop enables consistent adherence to institution-approved practice guidelines while maintaining traceability and transparency within the access-planning workflow.

Registration and Motion-Compensation Architecture

Figure 7A:
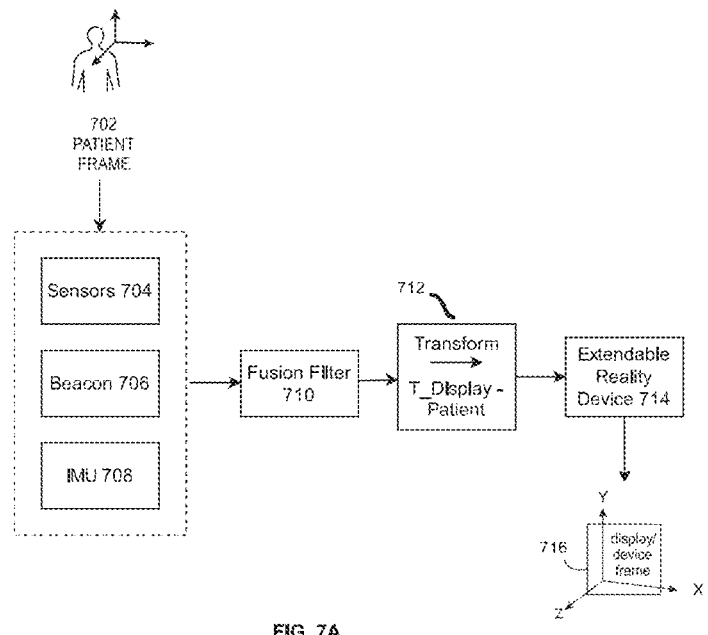
FIG. 7A illustrates a subsystem to transform a patient frame into a representative display frame, according to certain embodiments.

The registration subsystem 700 of FIG. 7A operates within the processing circuitry 116 of FIG. 1B. In particular, the fusion filter 710 is an implementation of, or a subcomponent within, the registration engine 124. The sensor block 704, beacon interface 706, and IMU 708 provide motion and geometry signals to the registration engine 124, which executes the fusion filter 710 to compute the transform 712 (Tdisplay←patient). The transform 712 is consumed by the overlay compositor 130 of FIG. 1B so that patient-registered graphics produced by the processing circuitry 116 remain spatially aligned in the extended-reality device 118.

Figure 7B:
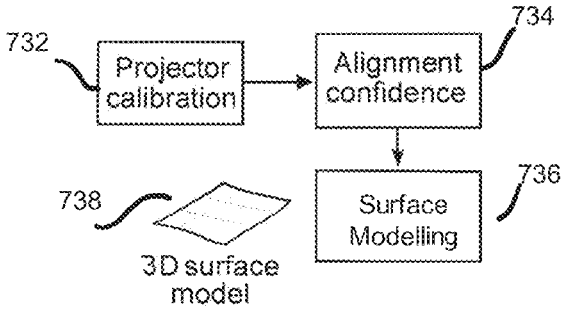
FIG. 7B illustrates a subsystem depicting projector calibration, surface modelling, and an alignment confidence metric, according to certain embodiments.
Figure 7C:
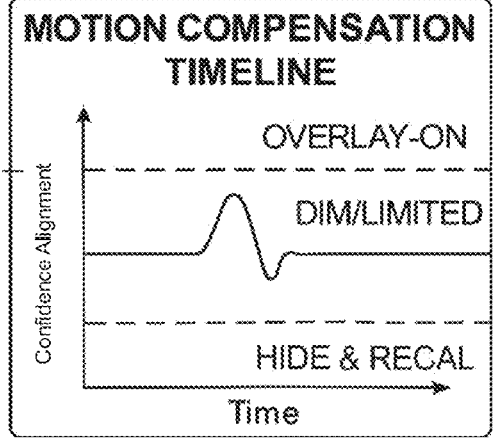
FIG. 7C illustrates a motion-compensation timeline in which alignment confidence is plotted versus time, according to certain embodiments.

FIGS. 7A-7C depict a registration and motion-compensation architecture that maintains adaptive overlay alignment between a patient coordinate frame and a display coordinate frame so that patient-registered graphics remain spatially correct in the extended-reality device.

As shown in FIG. 7A, a patient coordinate frame 702 is anchored to the anatomy by establishing a three-dimensional surface model of the region of interest. The surface model may be obtained by depth or structured-light sensing that acquires dense surface point clouds of skin topology and triangulates the points into a real-time mesh; by ultrasound probe localization in which the probe tip position and orientation are tracked using visual fiducials, inertial measurement units, or acoustic/ultrasound beacons; and by marker-based or markerless tracking that registers visible/infrared fiducials, skin texture, vascular patterns, or anatomical landmarks to camera or imaging frames. A sensor block 704, a beacon interface 706, and an IMU 708 provide geometry and motion signals to a fusion filter 710 within the registration engine 124 of FIG. 1B. The fusion filter 710 may be implemented as an extended or unscented Kalman filter or as a factor-graph optimizer that models sensor uncertainties and temporal delays and incorporates geometric refinement such as Iterative Closest Point alignment on the surface mesh to control drift. From these inputs the fusion filter 710 computes a continuously updated rigid-body (or affine) transformation 712, Tdisplay←patient, that maps any point Ppatient expressed in the patient frame into the display/device frame according to Pdisplay=TPD×Ppatient (Equation [T-PD-1]). The transformation is initialized by a brief calibration sequence and thereafter is updated at a rate of at least 30 Hz, typically 60 Hz or faster, using filtered IMU and depth/vision measurements.

The transform 712 is consumed by the overlay compositor 130 of FIG. 1B to render patient-registered graphics in the extended-reality device 118. When the head-worn display 132 is active, Tdisplay←patient is applied in the pass-through renderer. When the projection module 134 is active, Tdisplay←patient is combined with a projector calibration to generate a per-pixel warp that keeps projected content locked to curved skin. The observer output 138 receives a synchronized view based on the same transformation for external display. The upstream data products that supply anatomical content are produced in the pipeline of FIG. 3: modalities such as ultrasound 302-1, IR/NIR 302-2, photoacoustic 302-3, OCT 302-4, HSI 302-5, and LSCI 302-6 are preprocessed at 304, segmented at 306, and normalized to the patient frame at 308. The fusion engine 310 of FIG. 3 performs multimodal image fusion (e.g., early feature fusion 312 and late decision fusion 314) to improve anatomical inference, while the fusion filter 710 of FIG. 7A performs pose and registration fusion; both ultimately converge in the compositor 130, which places fused anatomical content using Tdisplay←patient. In tiered deployments introduced in FIG. 1B, the fusion filter 710 executes on the on-device runtime 142 for latency, while calibration updates, confidence estimation, and telemetry logging synchronize with an edge node 144 or cloud service 146 when connectivity allows.

FIG. 7B details projector calibration 730, surface modelling 732, and an alignment confidence metric 734. The projector calibration 730 determines intrinsic parameters (focal lengths, principal point, lens-distortion coefficients) and extrinsic parameters relating the projector optics to the display/device frame. Calibration may be derived by projecting structured-light or checkerboard patterns and observing them with a rigidly mounted camera, a head-worn camera, or an external camera, and by minimizing reprojection error over fiducials or Charuco/ArUco boards. In situ refinement may compare a projected lattice to depth/structured-light/LiDAR returns while the fusion filter 710 supplies the current Tdisplay←patient 712. The surface modelling 732 constructs and updates a three-dimensional surface model 738 of patient skin from depth/structured-light/LiDAR returns, stereo reconstruction, or a fused model seeded by prior imaging, and incorporates pose updates from the fusion filter so that the model remains registered to the patient frame during patient motion and device motion. The alignment confidence 734 is computed from residuals including reprojection error on the surface model 738, drift of tracked features over time, agreement between inertial predictions and vision-based pose updates, and photometric consistency of the projected pattern. The metric is supplied to the compositor to govern presentation state and to an auto-refresh trigger that initiates a fast calibration refresh when the metric falls below a preset value. In some embodiments the projection calibration is derived from the three-dimensional surface model 738 and is automatically refreshed when the alignment confidence 734 drops below a threshold; during refresh the display may dim and, where enabled, a brief haptic cue is provided to the operator.

FIG. 7C illustrates a motion-compensation timeline in which alignment confidence is plotted versus time with two thresholds that determine presentation states. When the metric is at or above an upper threshold, an overlay-on state renders patient-registered overlays through the head-worn display and projects overlays on skin via the projector using adaptive calibration. When the metric falls between the thresholds, a dim/limited state reduces overlay opacity or update rate while the fusion filter 710 and surface modelling 732 reconverge; per-pixel warps remain active. When the metric falls below a lower threshold, a hide-and-recal state inhibits overlay presentation and requests a quick recalibration; the auto-refresh trigger executes a short sequence and the system resumes full presentation once confidence again exceeds the thresholds.

The architecture compensates both patient and provider motion. Patient motion such as respiration or limb drift updates the surface model 738 and re-anchors overlay attachment points in the patient frame. Provider motion updates the display/device pose via the IMU 708; the compositor 130 adjusts viewpoint and projection frustum so overlays remain perceptually stationary on the anatomy. An illustrative use case is ultrasound-guided peripheral IV placement: the forearm surface is scanned by structured light to seed the patient frame; the ultrasound probe is localized by a small fiducial and an IMU so live B-mode frames share that frame; as the patient flexes the wrist, depth sensing updates the surface mesh and the fusion filter recomputes Tdisplay←patient at video rate so vein centerlines and access-planning graphics remain pinned to skin; if residual error exceeds approximately 3 mm RMS, the display briefly dims and a haptic tick prompts a one-second hold while calibration refreshes, after which the overlay returns to full brightness. This closed-loop behavior preserves spatial fidelity of the overlays across continuous motion and across on-device, edge-assisted, and cloud-assisted deployments.

Extended-Reality Presentation

Figure 8:
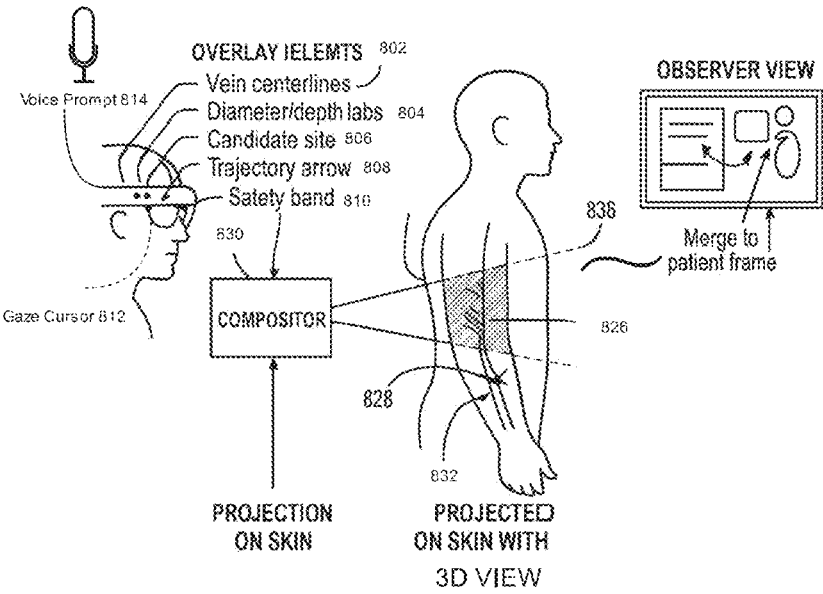
FIG. 8 is a schematic diagram illustrating an extended-reality presentation architecture, according to certain embodiments.

FIG. 8 is a schematic diagram illustrating an extended-reality presentation architecture 800, according to certain embodiments. The figure depicts three coordinated presentation paths: a head-worn display pass-through overlay, a projection-on-skin path with a surface-warped safety mask, and an observer/telepresence path with real-time remote annotation merge.

In the head-worn display path, a set of overlay elements 802 is rendered in a pass-through view 816 seen by an operator. The overlay elements 802 include diameter/depth labels 804 that encode quantitative measurements derived from upstream estimation, a candidate site indicator 806 that marks a computed access location, a trajectory arrow 808 that depicts an insertion direction vector toward a target depth, and a safety band 810 that visualizes policy-derived or anatomy-derived keep-in/keep-out regions. The pass-through view 816 further presents a gaze cursor 812 to enable hands-free selection and confirmation and provides a voice prompt 814 to support spoken commands and status cues. In operation, the pass-through view 816 receives a synchronized overlay stream from a compositor 830, described below, so that each of the overlay elements 802 is patient-registered and updated in real time.

In the projection-on-skin path, a projector device 820 projects graphics directly onto patient skin. The projector device 820 is driven by the compositor 830 and uses a three-dimensional surface model 828 to compute a per-pixel warp appropriate for curved anatomy. Under this calibration, the projector device 820 renders a projected safety mask 822 that excludes regions of low confidence or poor superficial venous contrast, a projected entry marker 824 that coincides with the candidate site indicator 806, and a depth ruler 826 that provides a visual gauge of insertion depth or target depth along the depicted trajectory arrow 808. The surface model 828 may be updated continuously from depth/structured-light/LiDAR sensing so that projected content remains aligned as the patient or device moves.

In the observer/telepresence path, an observer view 832 presents, to an external monitor or recorder, a synchronized view of the same patient-registered overlays that appear in the head-worn display path and on skin in the projection-on-skin path. A remote expert user interface 834 enables a remote participant to create annotation packets 836. The annotation packets 836 are encoded in patient-frame coordinates and supplied to a merge-to-patient-frame stage 838 that reconciles the remote annotations with the current registration state. The merged annotations are returned to the compositor 830, which redistributes them to the pass-through view 816 and to the projector device 820 so that remote guidance is rendered in place on the patient and in the operator's field of view.

The compositor 830 is a presentation and synchronization module configured to assemble overlay elements 802, encode patient-frame geometry derived from the surface model 828, and generate synchronized output streams for the pass-through view 816, the projector device 820, and the observer view 832. In one embodiment, the compositor 830 enforces presentation states based on alignment confidence from the registration engine: when confidence is nominal, full-fidelity overlays are rendered; when confidence drops below a threshold, overlay opacity or update rate is reduced or a recalibration prompt is issued before projection resumes.

Data-flow relationships in FIG. 8 are as follows. The surface model 828 supplies geometric information to the compositor 830 for projection warping. The compositor 830 outputs an HMD overlay stream to the pass-through view 816 with the overlay elements 802 (including the gaze cursor 812 and the voice prompt 814), a projection stream to the projector device 820 that yields the projected safety mask 822, the projected entry marker 824, and the depth ruler 826 on patient skin, and a mirrored stream to the observer view 832. The remote expert user interface 834 produces the annotation packets 836, which are merged to patient-frame coordinates at 838 and injected back into the compositor 830 for immediate redistribution to all presentation paths.

Hands-Free Interaction Subsystem

Figure 9:
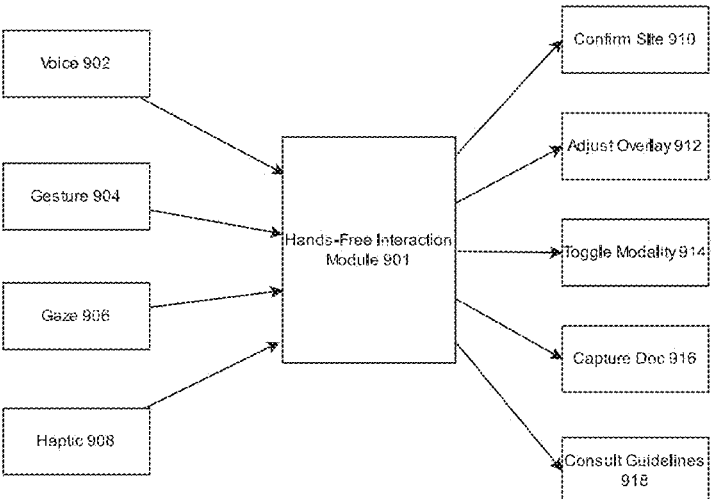
FIG. 9 is a block diagram illustrating a hands-free interaction subsystem, according to certain embodiments.

FIG. 9 is a block diagram illustrating a hands-free interaction subsystem 900, in accordance with embodiments of the present disclosure. As introduced with reference to FIG. 1*i*, an extended-reality device 118 includes an interaction module 134 and the processing circuitry 116 is configured to accept user actions that confirm a candidate access site, adjust overlay parameters, and change a capture configuration. FIG. 9 details these functions through a hands-free interaction module 901 that ingests voice input 902, gesture input 904, gaze input 906, and haptic input 908, and issues corresponding control actions comprising confirm site 910, adjust overlay 912, toggle modality 914, capture documentation 916, and consult guidelines 918. In various embodiments, the hands-free interaction module 901 executes on an on-device tier 142 of the head-worn display 132, on an edge node 144, or across both, with the command channel persisted over the network 140 and with an offline fallback mode that maintains local operation.

Voice input 902 denotes a microphone and speech interface configured to recognize command phrases within a sterile field. In one embodiment, voice input 902 implements keyword spotting and constrained grammars with far-field beamforming and noise suppression so that commands such as "confirm site," "increase label size," "toggle ultrasound," "capture snapshot," and "consult guidelines" are recognized with low latency. The hands-free interaction module 901 maps recognized intents to the actions 910 through 918 and forwards a structured message to the processing circuitry 116, which updates the overlay compositor 130, the imaging system 114 configuration, and the policy profile 126 as required.

Gesture input 904 denotes vision-based or depth-based recognition of operator hand and wrist poses as captured by the head-worn cameras or an auxiliary sensor. Gesture input 904 is configured to detect discrete selections and continuous adjustments. Examples include a pinch-and-dwell to confirm a highlighted candidate access site, a circular motion to adjust overlay opacity, a swipe to cycle imaging modalities, and a two-finger hold to trigger recalibration. Gesture input 904 includes temporal filtering and minimum duration thresholds so that inadvertent motions do not trigger actions.

Gaze input 906 denotes an eye-tracking and dwell-selection interface provided by the head-worn display 132. Gaze input 906 is configured to drive a gaze cursor, as depicted in FIG. 8, so that the practitioner can target overlay elements such as vein centerlines, depth labels, or entry markers. Dwell times and fixation stability thresholds are configurable. When a dwell confirmation criterion is satisfied, the hands-free interaction module 901 emits the corresponding action 910 or 912 with the selected overlay element's patient-frame coordinates, which the processing circuitry 116 uses to update the trajectory solver 610 and the overlay compositor 130.

Haptic input 908 denotes a tactile interface delivered by a wristband, ring, or headset actuator. Haptic input 908 is configured to acknowledge command receipt and to encode alignment confidence transitions. For example, a triple pulse affirms the confirm site action 910, a short pulse indicates an overlay parameter change 912, and a long pulse alerts the user when alignment confidence falls below a threshold as described in FIGS. 7B and 7C. The same accessory can accept tap patterns as an input channel that the hands-free interaction module 901 interprets as toggle modality 914 or capture documentation 916.

Confirm site 910 is a control action that commits a candidate access site selected via voice input 902, gesture input 904, or gaze input 906. The processing circuitry 116 records the selected skin entry point, the associated direction vector, and the target depth computed by the trajectory solver 610, and updates the overlays to reflect a locked plan. The clinical interface of FIG. 1B logs the committed site with timestamps, operator identifiers, and device metadata, and encodes the selection within the procedure record.

Adjust overlay 912 is a control action that modifies presentation parameters in the overlay compositor 130. Examples include changes to label size, color scale, opacity, safety-band visibility, and update rate. Adjust overlay 912 is constrained by the policy profile 126 so that safety-critical overlays remain visible or gated by alignment confidence when required by institutional policy.

Toggle modality 914 is a control action that changes a capture configuration of the imaging system 114. In one embodiment, toggle modality 914 cycles among ultrasound, near-infrared, infrared, photoacoustic imaging, optical coherence tomography, hyperspectral imaging, and laser speckle contrast imaging, or switches presets within a modality such as ultrasound depth or Doppler enablement. The hands-free interaction module 901 issues the request and the processing circuitry 116 reconfigures acquisition, preprocessing, and segmentation without breaking overlay continuity.

Capture documentation 916 is a control action that acquires audit media and metadata for clinical records. In one embodiment, capture documentation 916 saves a synchronized observer view as in FIG. 8, captures a still image of the insertion or incision site from an associated camera, associates spatial coordinates, timestamps, and operator identifiers, and uploads an annotated record to an electronic health record via the clinical interface. When a projection module is active, capture documentation 916 can also store a projection-aligned screenshot and the current alignment confidence for traceability.

Consult guidelines 918 is a control action that retrieves institution-approved policy bundles and surfaces context-specific recommendations. Upon invocation, the hands-free interaction module 901 requests the active institutional policy profile 602 and causes an explainer panel 606, as depicted in FIG. 6, to render a justification for acceptance or suppression of a candidate plan. The processing circuitry 116 logs the profile name and version and writes the event to an audit log 608 together with the evaluated constraints.

In operation, the voice input 902, the gesture input 904, the gaze input 906, and the haptic input 908 stream intents to the hands-free interaction module 901. The hands-free interaction module 901 translates these intents into the control actions confirm site 910, adjust overlay 912, toggle modality 914, capture documentation 916, and consult guidelines 918, which are consumed by the processing circuitry 116, the overlay compositor 130, the imaging system 114, and the clinical interface. Safety gating uses the alignment confidence described in FIGS. 7B and 7C so that, when confidence drops below a preset value, presentation is inhibited or dimmed and confirmations are deferred until recalibration completes. This subsystem enables sterile, low-latency interaction that is literally aligned with the claimed capabilities for voice commands, gesture recognition, gaze selection, haptic input, and acceptance of user actions that affect access-site confirmation, overlay parameters, and capture configuration.

Clinical Documentation Capture Subsystem

Figure 10:
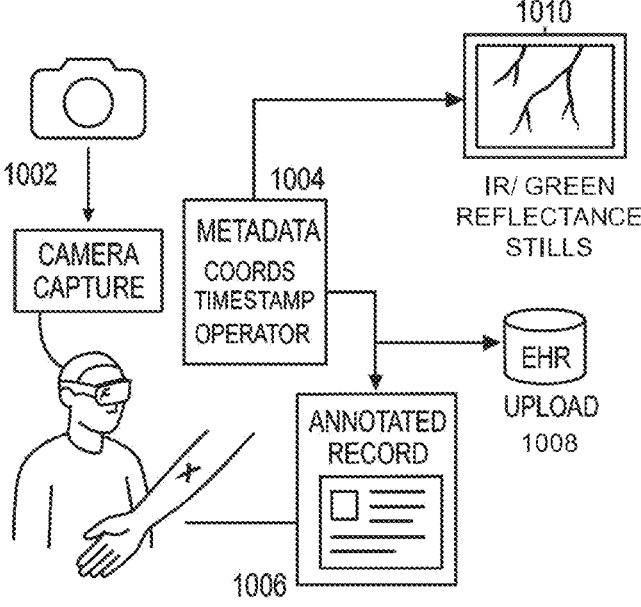
FIG. 10 is a block diagram illustrating a clinical documentation capture subsystem, according to certain embodiments.

FIG. 10 is a block diagram illustrating a clinical documentation capture subsystem 1000, in accordance with embodiments of the present disclosure. The subsystem generates procedure records that include images of an insertion or incision site, associated spatial and temporal metadata, and optional optical reflectance stills, and transmits the resulting annotated record to an electronic health record.

A camera capture 1002 is configured to capture an image of an insertion or incision site on a patient. In various embodiments, the camera capture 1002 is provided by a camera integrated in an extended-reality unit, a companion mobile device, or a room camera positioned to view the operative field. The capture may be initiated by a hands-free command or automatically upon confirmation of a candidate access site. The captured frame can include an operator's view, a projection-aligned screenshot, or a close-range photograph of the skin region.

A metadata block 1004 associates the captured image with spatial coordinates, timestamps, and operator identifiers. Spatial coordinates are expressed in a patient coordinate frame obtained from the registration pipeline and may include the skin entry point, a direction vector, and a target depth that were computed during access planning. The metadata block 1004 further records imaging modalities in use and presentation parameters active at the time of capture so that downstream review can reconstruct context.

An annotated record 1006 is produced by compositing the captured image with patient-registered overlays that may include vein centerlines, diameter and depth labels, a candidate access site marker, a trajectory arrow, and a safety band. The annotated record 1006 embeds the metadata from the metadata block 1004 and forms a persistent document suitable for clinical audit and quality improvement.

An EHR upload 1008 is configured to upload the annotated record 1006 to an electronic health record through a clinical interface. The upload includes the image, the spatial coordinates, the timestamps, the operator identifiers, and the modality and presentation descriptors. In certain embodiments, if network connectivity is degraded, the upload is deferred and synchronized when connectivity is restored.

A reflectance stills path 1010 operates in parallel with the camera capture 1002. The subsystem acquires infrared or green-light reflectance stills that enhance superficial venous visibility, co-registers the stills to the patient coordinate frame, and submits the resulting images to the EHR upload 1008. The reflectance stills path 1010 supports generation of a projected safety mask and provides documentation that the visual contrast used for guidance was present at the recorded site.

In operation, the camera capture 1002 provides the source image, the metadata block 1004 attaches coordinates, timestamps, and operator identifiers, the annotated record 1006 is created with patient-registered overlays, and the EHR upload 1008 transmits the record to the electronic health record. In parallel, the reflectance stills path 1010 provides infrared or green-light frames that are likewise uploaded via the EHR upload 1008. This subsystem literally captures an image of an insertion or incision site, associates the image with spatial coordinates, timestamps, and operator identifiers, and uploads an annotated record to an electronic health record, with optional co-registered reflectance stills preserved for longitudinal visualization.

Real-Time Remote Guidance Based on Telemedicine

Figure 11:
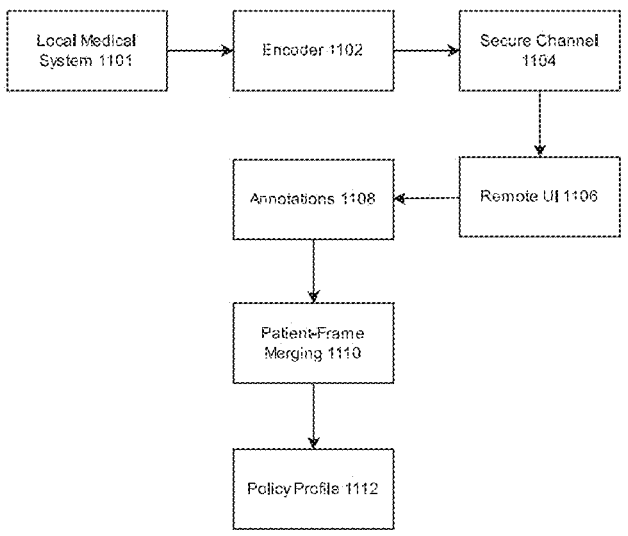
FIG. 11 illustrates exemplary end-to-end operation cycles for real-time remote guidance based on Telemedicine pipeline, according to certain embodiments.

FIG. 11 illustrates exemplary end-to-end operation cycles for real-time remote guidance based on Telemedicine pipeline. The constituent blocks that include, but may not be limited to, an encoder 1102, a secure channel 1104, a remote user interface 1106, annotations 1108, a patient-frame merging module 1110, and a policy profile 1112.

An observer view together with vector overlays is encoded at the encoder 1102, which packages the view using a low-latency codec such as H.264/AVC, H.265/HEVC, or AV1 and time-aligns overlay vectors and telemetry as metadata. The encoded stream is transmitted over the secure channel 1104 using authenticated encryption—for example TLS 1.3 with ECDHE key exchange and AES-GCM, or DTLS-SRTP with per-packet AES-128/256-GCM. In some deployments a QUIC transport with TLS 1.3 provides congestion control, connection migration, and 0-RTT resumption; keys are rotated to maintain perfect forward secrecy, certificates are pinned, and mutual TLS authenticates devices.

At the remote user interface 1106 the incoming view is rendered and tools are presented for freehand strokes, geometric shapes, text labels, and templated cues. The remote user interface 1106 emits annotations 1108 stamped with millisecond timestamps and returns them through the secure channel 1104. Upon receipt, patient-frame merging 1110 transforms each annotation from the remote screen space into the patient coordinate frame by applying the current registration transform maintained by the local system. The merged content passes through the policy profile 1112, which applies role and site policy (for example, filtering trainee notes from the operator's view) and records identity, time, and active profile version in the procedure record before redistribution to the head-worn display and projector.

In a low-bandwidth clinic, the encoder 1102 operates in adaptive-bitrate mode at approximately 360p-720p with targets from about 300 kbps to 2 Mbps and may use scalable video coding layers. The secure channel 1104 enables loss recovery using selective retransmission and forward-error correction (for example, RTP FlexFEC or Reed-Solomon parity). The remote user interface 1106 constrains jitter buffers to roughly 20-120 ms so that the round-trip latency for annotations 1108 remains below about 200 ms, allowing cues to appear "stuck" to the anatomy. If bandwidth degrades further, the system falls back to an overlays-only mode wherein the encoder 1102 transmits vector overlays and occasional keyframes while pausing full-motion video; patient-frame merging 1110 continues to anchor cues, and policy profile 1112 signals the reduced-video state.

In a multi-party consult, several instances of the remote user interface 1106 join via the secure channel 1104, optionally through a relay or selective-forwarding unit while retaining end-to-end encryption. Patient-frame merging 1110 arbitrates concurrent annotations 1108 by time and priority, supports layered channels (for example, ultrasound fellow, attending, radiology), and resolves conflicts by last-writer-wins or explicit acceptance by the local operator. The policy profile 1112 enforces viewer-specific visibility and maintains a comprehensive audit log.

In an on-premises residency deployment, the secure channel 1104 terminates inside a facility network segment to satisfy data-residency requirements; inter-building links may use IPsec or WireGuard tunnels with AES-GCM and periodic re-keying. Identity tokens (for example, OAuth 2.0/OpenID Connect with short-lived access tokens) bind users to roles consumed by the policy profile 1112. The encoder 1102 may publish a high-resolution archival stream for later review alongside a low-latency stream for the live conference, with synchronized annotation timelines.

In intermittent connectivity, the encoder 1102 captures snapshots and short clips together with overlay state and persists them encrypted at rest using AES-256-GCM with per-record keys. When connectivity returns, the secure channel 1104 uploads the bundle; the remote user interface 1106 annotates asynchronously; patient-frame merging 1110 applies the queued annotations when the local session resumes; the policy profile 1112 records which guideline profile version was active when each annotation was applied.

In a cross-vendor arrangement, the encoder 1102 on an OEM imaging console publishes DICOM secondary-capture frames in parallel with a low-latency stream. The secure channel 1104 negotiates NAT traversal via ICE with STUN/TURN; media uses SRTP with AES-GCM while control messages use TLS 1.3. The remote user interface 1106 runs in a browser or tablet; annotations 1108 may include "avoid zone" polygons, diameter arrows, and textual prompts. Patient-frame merging 1110 maps these cues to the patient frame and returns them both to the console and to the extended-reality device; the policy profile 1112 redacts protected identifiers from mirrored views.

An illustrative cycle proceeds as follows: a nurse begins a session; the encoder 1102 starts 720p30 capture and transmits via the secure channel 1104. A remote expert draws a trajectory arrow and types "shift 5 mm lateral"; the annotations 1108 are time-stamped and returned. Patient-frame merging 1110 places the arrow on skin at the intended location using the current registration; the policy profile 1112 verifies the expert's role, allows display, and logs the event. If alignment confidence dips below a threshold during patient motion, local rendering temporarily dims overlays and the remote user interface 1106 receives the status; once confidence recovers, full overlays resume without losing remote annotations.

Security details include TLS 1.3 ciphers such as ECDHE-RSA-AES-256-GCM-SHA384 on the secure channel 1104, device certificate pinning, mutual TLS, and DTLS-SRTP with periodic SRTP key refresh for media. Integrity of annotations 1108 may be protected with detached Ed25519 signatures verified before acceptance by patient-frame merging 1110. Locally cached frames and timelines remain sealed with AES-256-GCM, with keys derived via HKDF from device secrets and session nonces.

Physiotherapy Application

Figure 12:
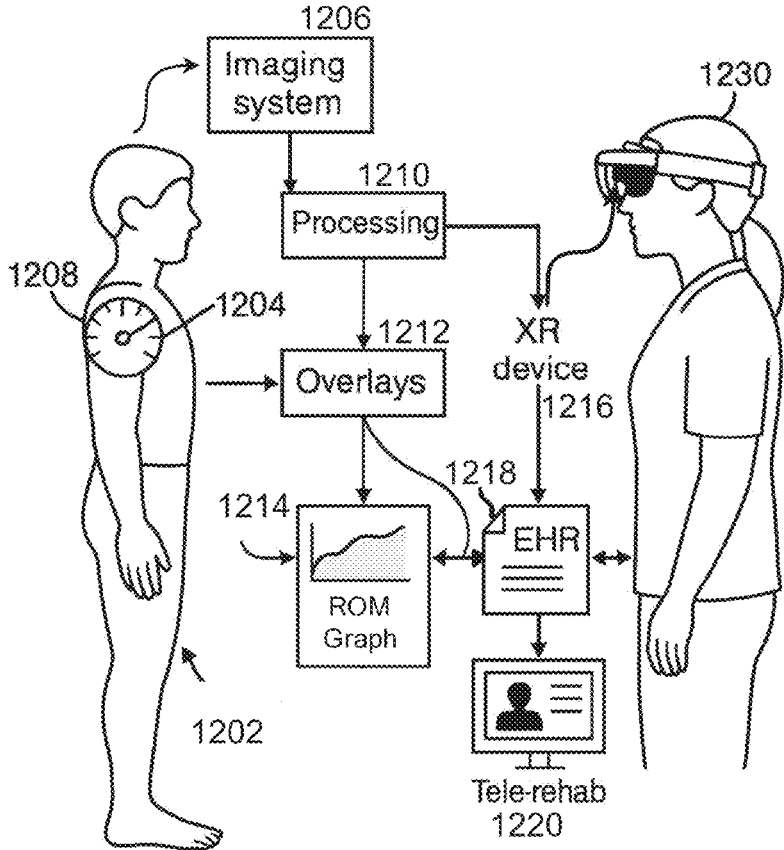
FIG. 12 depicts a schematic of the system application for physiotherapy, according to certain embodiments.

FIG. 12 depicts a schematic of the system application for physiotherapy. To aid understanding of FIG. 12 in a clinical setting, the following non-limiting illustrations show how the same capture, processing, and extended-reality rendering subsystems (imaging system 1206, processing circuitry 1210, overlays 1212, extended-reality device 1216, ROM graph 1214, and EHR 1218) operate during two common physiotherapy use cases.

In one embodiment, a patient 1202 recovering from a tibial fracture begins gait retraining. The imaging system 1206 acquires depth and inertial streams as the patient steps along a marked pathway. The processing circuitry 1210 constructs a live musculoskeletal model, estimates hip-knee-ankle joint angles and temporo-spatial gait parameters, and updates the ROM graph 1214 with stride length, cadence, stance time, and symmetry indices. The extended-reality device 1216 presents overlays 1212 aligned to the limb: a knee-flexion gauge 1204 with a target band of 70-90 degrees for early-phase sit-to-stand, trajectory arrows indicating foot placement, and a safety mask over valgus positions exceeding a therapist-set threshold. When the patient drifts into hip adduction or knee valgus, the processing circuitry 1210 generates a corrective cue 1208 such as "move knee outward" or an arrow guiding neutral alignment. If the patient or clinician changes position, adaptive overlay alignment maintains registration; when an alignment confidence metric dips, overlays dim until a quick recalibration completes, then resume at full fidelity. At the end of the set, the system stores a session record to the EHR 1218 including angle traces, stride-to-stride symmetry, repetition counts, pain scores verbally captured through the head-worn device, and screenshots of key frames. For at-home exercises, the same overlays 1212 render via the extended-reality device 1216 while a synchronized observer view is available through tele-rehab 1220; a remote therapist can annotate footfall targets, which are merged back into the patient frame and displayed in-band.

In another embodiment, a patient 1202 performs scapular-plane abduction. The imaging system 1206 captures torso and arm kinematics without markers. The processing circuitry 1210 binds a joint-angle gauge 1204 to the glenohumeral joint and updates the ROM graph 1214 with repetitions, peak angle, hold time at 90 degrees, and tempo. The extended-reality device 1216 renders overlays 1212 that include a target band of 90-110 degrees, a trajectory arrow guiding the plane of motion, and posture cues that flag trunk lean or shoulder hiking. If form deviates, the processing circuitry 1210 issues a corrective cue 1208 such as "reduce trunk compensation" or "slow tempo." When the patient approaches a pain-limited range, the overlay safety mask narrows the allowable band; if the patient exceeds a clinician-defined limit, visualization inhibits and a recalibration or rest prompt appears. The EHR 1218 is updated with angle and velocity curves, set/rep structure, compliance to targets, and any therapist annotations. During tele-rehab 1220, a remote therapist draws an arc indicating the desired end range; the annotation is encoded in the patient coordinate frame, merged into the overlays 1212, and rendered to both the patient and the supervising clinician wearing the head-worn display 1230.

Across both scenarios, the processing circuitry 1210 personalizes goals from a policy or goal profile, recommends progression rules based on recent performance trends recorded in the ROM graph 1214, and maintains adaptive overlay alignment so that gauges, target bands, trajectory arrows, posture cues, and any safety mask remain perceptually stationary on the relevant anatomy while data and annotated records are written to the EHR 1218.

Artificial Intelligence System Implementation

The system described in conjunction with FIG. 1B comprises one or more subsystems based on Artificial Intelligence. Implementation of the subsystems based on the Artificial Subsystems is illustrated by FIGS. 13 to 23.

Some implementations of the technology disclosed relate to using a Transformer model to provide an AI system. In particular, the technology disclosed proposes a parallel input, parallel output (PIPO) AI system based on the Transformer architecture. The Transformer model relies on a self-attention mechanism to compute a series of context-informed vector-space representations of elements in the input sequence and the output sequence, which are then used to predict distributions over subsequent elements as the model predicts the output sequence element-by-element. Not only is this mechanism straightforward to parallelize, but as each input's representation is also directly informed by all other inputs' representations, this results in an effectively global receptive field across the whole input sequence.

This stands in contrast to, e.g., convolutional architectures which typically only have a limited receptive field.

In one implementation, the disclosed AI system is a multilayer perceptron (MLP). In another implementation, the disclosed AI system is a feedforward neural network. In yet another implementation, the disclosed AI system is a fully connected neural network. In a further implementation, the disclosed AI system is a fully convolution neural network. In a yet further implementation, the disclosed AI system is a semantic segmentation neural network. In a yet another further implementation, the disclosed AI system is a generative adversarial network (GAN) (e.g., CycleGAN, StyleGAN, pixelRNN, text-2-image, DiscoGAN, IsGAN). In a yet another implementation, the disclosed AI system includes self-attention mechanisms like Transformer, Vision Transformer (ViT), Bidirectional Transformer (BERT), Detection Transformer (DETR), Deformable DETR, UP-DETR, DeiT, Swin, GPT, iGPT, GPT-2, GPT-3, various ChatGPT versions, various LLaMA versions, BERT, Span-BERT, RoBERTa, XLNet, ELECTRA, UniLM, BART, T5, ERNIE (THU), KnowBERT, DeiT-Ti, DeiT-S, DeiT-B, T2T-ViT-14, T2T-ViT-19, T2T-ViT-24, PVT-Small, PVT-Medium, PVT-Large, TNT-S, TNT-B, CPVT-S, CPVT-S-GAP, CPVT-B, Swin-T, Swin-S, Swin-B, Twins-SVT-S, Twins-SVT-B, Twins-SVT-L, Shuffle-T, Shuffle-S, Shuffle-B, XCiT-S12/16, CMT-S, CMT-B, VOLO-D1, VOLO-D2, VOLO-D3, VOLO-D4, MoCo v3, ACT, TSP, Max-Deep-Lab, VisTR, SETR, Hand-Transformer, HOT-Net, METRO, Image Transformer, Taming transformer, TransGAN, IPT, TTSR, STTN, Masked Transformer, CLIP, DALL-E, Cogview, UniT, ASH, TinyBert, FullyQT, ConvBert, FCOS, Faster R-CNN+FPN, DETR-DC5, TSP-FCOS, TSP-RCNN, ACT+MKDD (L=32), ACT+MKDD (L=16), SMCA, Efficient DETR, UP-DETR, UP-DETR, ViTB/16-FRCNN, ViT-B/16-FRCNN, PVT-Small+RetinaNet, Swin-T+RetinaNet, Swin-T+ATSS, PVT-Small+DETR, TNT-S+DETR, YOLOS-Ti, YOLOS-S, and YOLOS-B.

In one implementation, the disclosed AI system is a convolution neural network (CNN) with a plurality of convolution layers. In another implementation, the disclosed AI system is a recurrent neural network (RNN) such as a long short-term memory network (LSTM), bi-directional LSTM (Bi-LSTM), or a gated recurrent unit (GRU). In yet another implementation, the disclosed AI system includes both a CNN and an RNN.

In yet other implementations, the disclosed AI system can use 1D convolutions, 2D convolutions, 3D convolutions, 4D convolutions, 5D convolutions, dilated or atrous convolutions, transpose convolutions, depthwise separable convolutions, pointwise convolutions, 1×1 convolutions, group convolutions, flattened convolutions, spatial and cross-channel convolutions, shuffled grouped convolutions, spatial separable convolutions, and deconvolutions. The disclosed AI system can use one or more loss functions such as logistic regression/log loss, multi-class cross-entropy/softmax loss, binary cross-entropy loss, mean-squared error loss, L1 loss, L2 loss, smooth L1 loss, and Huber loss. The disclosed AI system can use any parallelism, efficiency, and compression schemes such TFRecords, compressed encoding (e.g., PNG), sharding, parallel calls for map transformation, batching, prefetching, model parallelism, data parallelism, and synchronous/asynchronous stochastic gradient descent (SGD). The disclosed AI system can include upsampling layers, downsampling layers, recurrent connections, gates and gated memory units (like an LSTM or GRU), residual blocks, residual connections, highway connections, skip connections, peephole connections, activation functions (e.g., non-linear transformation functions like rectifying linear unit (ReLU), leaky ReLU, exponential liner unit (ELU), sigmoid and hyperbolic tangent (tanh)), batch normalization layers, regularization layers, dropout, pooling layers (e.g., max or average pooling), global average pooling layers, and attention mechanisms.

The disclosed AI system can be a linear regression model, a logistic regression model, an Elastic Net model, a support vector machine (SVM), a random forest (RF), a decision tree, and a boosted decision tree (e.g., XGBoost), or some other tree-based logic (e.g., metric trees, kd-trees, R-trees, universal B-trees, X-trees, ball trees, locality sensitive hashes, and inverted indexes). The disclosed AI system can be an ensemble of multiple models, in some implementations.

In some implementations, the disclosed AI system can be trained using backpropagation-based gradient update techniques. Example gradient descent techniques that can be used for training the disclosed AI system include stochastic gradient descent, batch gradient descent, and mini-batch gradient descent. Some examples of gradient descent optimization algorithms that can be used to train the disclosed AI system are Momentum, Nesterov accelerated gradient, Adagrad, Adadelta, RMSprop, Adam, AdaMax, Nadam, and AMSGrad.

Transformer Logic

Machine learning is the use and development of computer systems that can learn and adapt without following explicit instructions, by using algorithms and statistical models to analyze and draw inferences from patterns in data. Some of the state-of-the-art models use Transformers, a more powerful and faster model than neural networks alone. Transformers originate from the field of natural language processing (NLP), but can be used in computer vision and many other fields. Neural networks process input in series and weight relationships by distance in the series. Transformers can process input in parallel and do not necessarily weigh by distance. For example, in natural language processing, neural networks process a sentence from beginning to end with the weights of words close to each other being higher than those further apart. This leaves the end of the sentence very disconnected from the beginning causing an effect called the vanishing gradient problem. Transformers look at each word in parallel and determine weights for the relationships to each of the other words in the sentence. These relationships are called hidden states because they are later condensed for use into one vector called the context vector. Transformers can be used in addition to neural networks. This architecture is described here.

Encoder-Decoder Architecture

Figure 13:
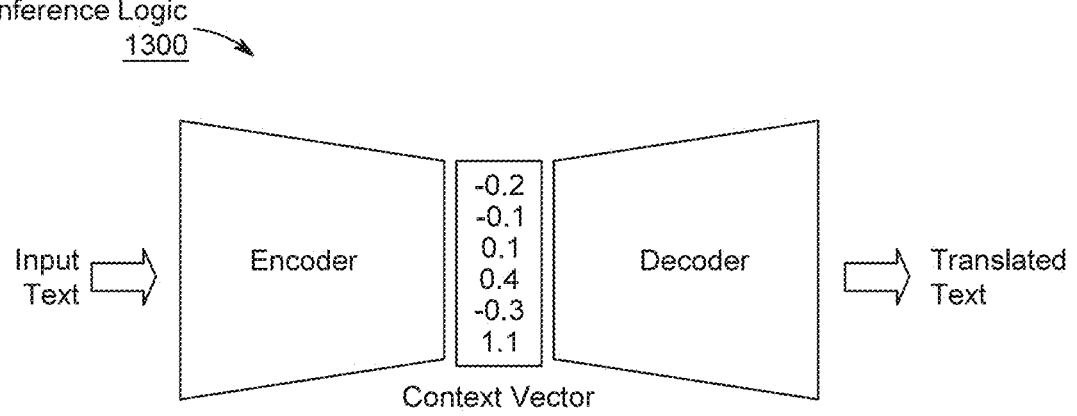
FIG. 13 is a schematic representation of an encoder-decoder architecture.

FIG. 13 is a schematic representation of an encoder-decoder architecture. This architecture is often used for NLP and has two main building blocks. The first building block is the encoder that encodes an input into a fixed-size vector. In the system we describe here, the encoder is based on a recurrent neural network (RNN). At each time step, t, a hidden state of time step, t−1, is combined with the input value at time step t to compute the hidden state at timestep t. The hidden state at the last time step, encoded in a context vector, contains relationships encoded at all previous time steps. For NLP, each step corresponds to a word. Then the context vector contains information about the grammar and the sentence structure. The context vector can be considered a low-dimensional representation of the entire input space. For NLP, the input space is a sentence, and a training set consists of many sentences.

The context vector is then passed to the second building block, the decoder. For translation, the decoder has been trained on a second language. Conditioned on the input context vector, the decoder generates an output sequence. At each time step, t, the decoder is fed the hidden state of time step, t−1, and the output generated at time step, t−1. The first hidden state in the decoder is the context vector, generated by the encoder. The context vector is used by the decoder to perform the translation.

The whole model is optimized end-to-end by using backpropagation, a method of training a neural network in which the initial system output is compared to the desired output and the system is adjusted until the difference is minimized. In backpropagation, the encoder is trained to extract the right information from the input sequence, the decoder is trained to capture the grammar and vocabulary of the output language. This results in a fluent model that uses context and generalizes well. When training an encoder-decoder model, the real output sequence is used to train the model to prevent mistakes from stacking. When testing the model, the previously predicted output value is used to predict the next one.

When performing a translation task using the encoder-decoder architecture, all information about the input sequence is forced into one vector, the context vector. Information connecting the beginning of the sentence with the end is lost, the vanishing gradient problem. Also, different parts of the input sequence are important for different parts of the output sequence, information that cannot be learned using only RNNs in an encoder-decoder architecture.

Attention Mechanism

Figure 14:
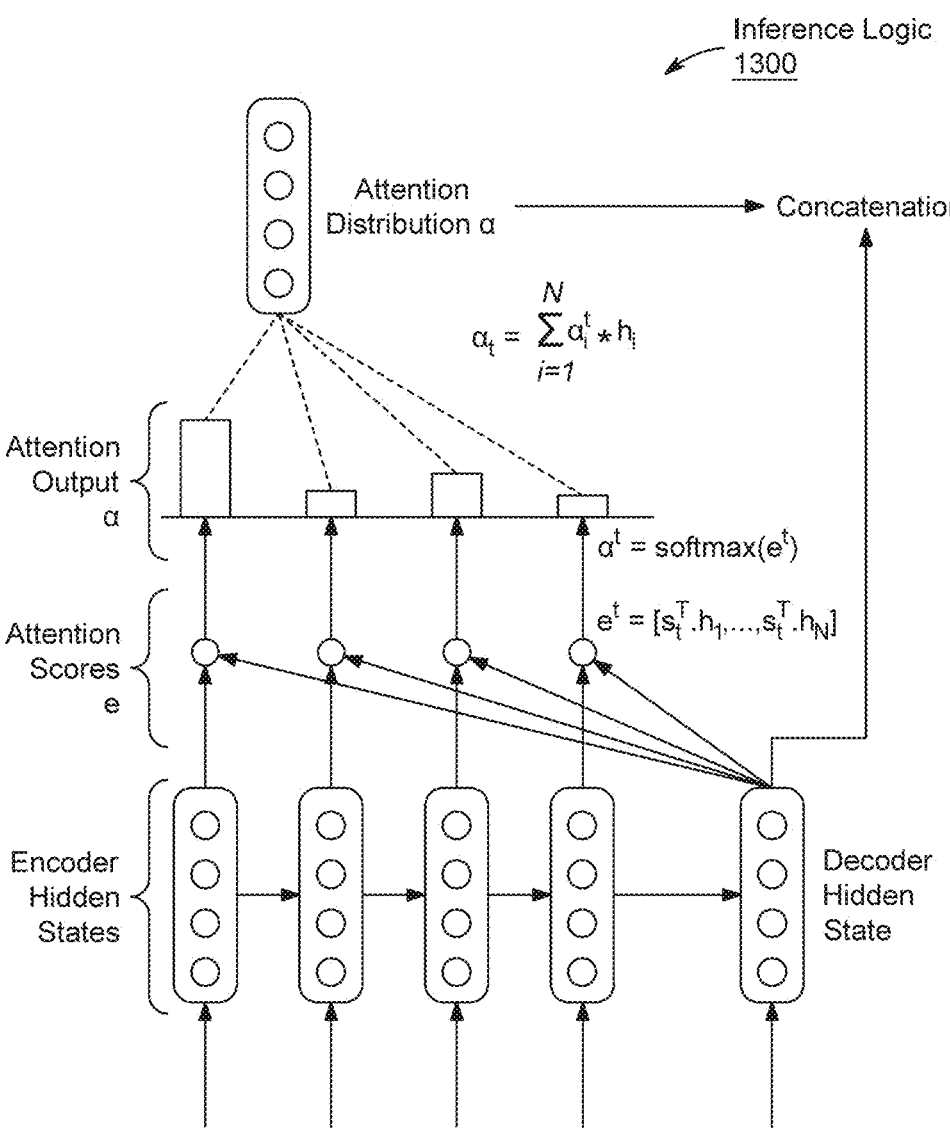
FIG. 14 shows an overview of an attention mechanism added onto an RNN encoder-decoder architecture.

Attention mechanisms distinguish Transformers from other machine learning models. The attention mechanism provides a solution for the vanishing gradient problem. FIG. 14 shows an overview of an attention mechanism added onto an RNN encoder-decoder architecture. At every step, the decoder is given an attention score, e, for each encoder hidden state. In other words, the decoder is given weights for each relationship between words in a sentence. The decoder uses the attention score concatenated with the context vector during decoding. The output of the decoder at time step t is based on all encoder hidden states and the attention outputs. The attention output captures the relevant context for time step t from the original sentence. Thus, words at the end of a sentence may now have a strong relationship with words at the beginning of the sentence. In the sentence "The quick brown fox, upon arriving at the doghouse, jumped over the lazy dog," fox and dog can be closely related despite being far apart in this complex sentence.

To weight encoder hidden states, a dot product between the decoder hidden state of the current time step, and all encoder hidden states, is calculated. This results in an attention score for every encoder hidden state. The attention scores are higher for those encoder hidden states that are similar to the decoder hidden state of the current time step. Higher values for the dot product indicate the vectors are pointing more closely in the same direction. The attention scores are converted to fractions that sum to one using the SoftMax function.

The SoftMax scores provide an attention distribution. The x-axis of the distribution is position in a sentence. The y-axis is attention weight. The scores show which encoder hidden states are most closely related. The SoftMax scores specify which encoder hidden states are the most relevant for the decoder hidden state of the current time step.

The elements of the attention distribution are used as weights to calculate a weighted sum over the different encoder hidden states. The outcome of the weighted sum is called the attention output. The attention output is used to predict the output, often in combination (concatenation) with the decoder hidden states. Thus, both information about the inputs, as well as the already generated outputs, can be used to predict the next outputs.

By making it possible to focus on specific parts of the input in every decoder step, the attention mechanism solves the vanishing gradient problem. By using attention, information flows more directly to the decoder. It does not pass through many hidden states. Interpreting the attention step can give insights into the data. Attention can be thought of as a soft alignment. The words in the input sequence with a high attention score align with the current target word. Attention describes long-range dependencies better than RNN alone. This enables analysis of longer, more complex sentences.

The attention mechanism can be generalized as: given a set of vector values and a vector query, attention is a technique to compute a weighted sum of the vector values, dependent on the vector query. The vector values are the encoder hidden states, and the vector query is the decoder hidden state at the current time step.

The weighted sum can be considered a selective summary of the information present in the vector values. The vector query determines on which of the vector values to focus. Thus, a fixed-size representation of the vector values can be created, in dependence upon the vector query.

The attention scores can be calculated by the dot product, or by weighing the different values (multiplicative attention).

Embeddings

For most machine learning models, the input to the model needs to be numerical. The input to a translation model is a sentence, and words are not numerical. multiple methods exist for the conversion of words into numerical vectors. These numerical vectors are called the embeddings of the words. Embeddings can be used to convert any type of symbolic representation into a numerical one.

Embeddings can be created by using one-hot encoding. The one-hot vector representing the symbols has the same length as the total number of possible different symbols. Each position in the one-hot vector corresponds to a specific symbol. For example, when converting colors to a numerical vector, the length of the one-hot vector would be the total number of different colors present in the dataset. For each input, the location corresponding to the color of that value is one, whereas all the other locations are valued at zero. This works well for working with images. For NLP, this becomes problematic, because the number of words in a language is very large. This results in enormous models and the need for a lot of computational power. Furthermore, no specific information is captured with one-hot encoding. From the numerical representation, it is not clear that orange and red are more similar than orange and green. For this reason, other methods exist.

A second way of creating embeddings is by creating feature vectors. Every symbol has its specific vector representation, based on features. With colors, a vector of three elements could be used, where the elements represent the amount of yellow, red, and/or blue needed to create the color. Thus, all colors can be represented by only using a vector of three elements. Also, similar colors have similar representation vectors.

For NLP, embeddings based on context, as opposed to words, are small and can be trained. The reasoning behind this concept is that words with similar meanings occur in similar contexts. Different methods take the context of words into account. Some methods, like GloVe, base their context embedding on co-occurrence statistics from corpora (large texts) such as Wikipedia. Words with similar co-occurrence statistics have similar word embeddings. Other methods use neural networks to train the embeddings. For example, they train their embeddings to predict the word based on the context (Common Bag of Words), and/or to predict the context based on the word (Skip-Gram). Training these contextual embeddings is time intensive. For this reason, pre-trained libraries exist. Other deep learning methods can be used to create embeddings. For example, the latent space of a variational autoencoder (VAE) can be used as the embedding of the input. Another method is to use 1D convolutions to create embeddings. This causes a sparse, high-dimensional input space to be converted to a denser, low-dimensional feature space.

Self-Attention: Queries (Q), Keys (K), Values (V)

Transformer models are based on the principle of self-attention. Self-attention allows each element of the input sequence to look at all other elements in the input sequence and search for clues that can help it to create a more meaningful encoding. It is a way to look at which other sequence elements are relevant for the current element. The Transformer can grab context from both before and after the currently processed element.

When performing self-attention, three vectors need to be created for each element of the encoder input: the query vector (Q), the key vector (K), and the value vector (V). These vectors are created by performing matrix multiplications between the input embedding vectors using three unique weight matrices.

After this, self-attention scores are calculated. When calculating self-attention scores for a given element, the dot products between the query vector of this element and the key vectors of all other input elements are calculated. To make the model mathematically more stable, these self-attention scores are divided by the root of the size of the vectors. This has the effect of reducing the importance of the scalar thus emphasizing the importance of the direction of the vector. Just as before, these scores are normalized with a SoftMax layer. This attention distribution is then used to calculate a weighted sum of the value vectors, resulting in a vector z for every input element. In the attention principle explained above, the vector to calculate attention scores and to perform the weighted sum was the same, in self-attention two different vectors are created and used. As the self-attention needs to be calculated for all elements (thus a query for every element), one formula can be created to calculate a Z matrix. The rows of this Z matrix are the z vectors for every sequence input element, giving the matrix a size length sequence dimension QKV.

Figure 15:
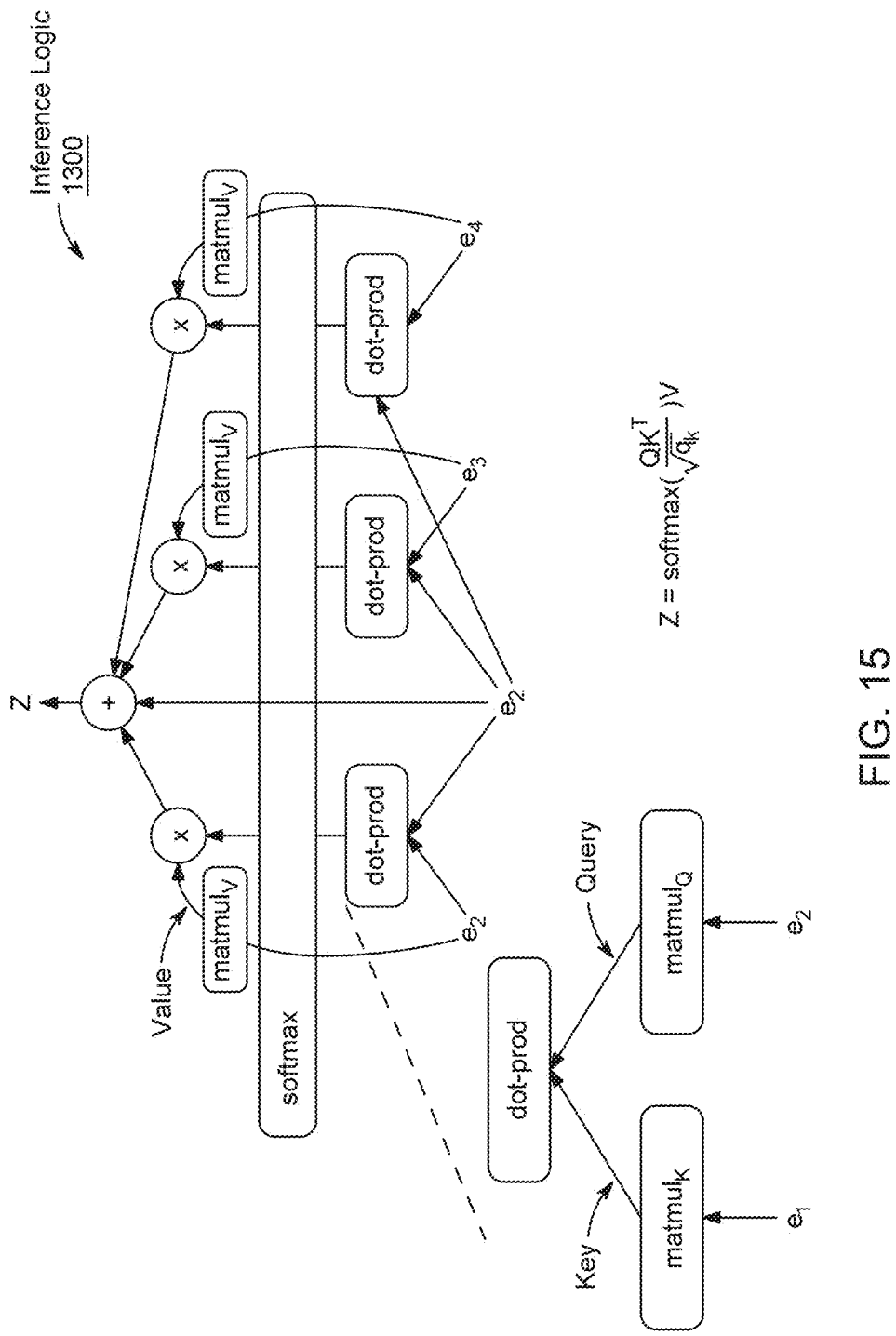
FIG. 15 is a schematic representation of the calculation of self-attention showing one attention head.

Multi-headed attention is executed in the Transformer. FIG. 15 is a schematic representation of the calculation of self-attention showing one attention head. For every attention head, different weight matrices are trained to calculate Q, K, and V. Every attention head outputs a matrix Z. Different attention heads can capture different types of information. The different Z matrices of the different attention heads are concatenated. This matrix can become large when multiple attention heads are used. To reduce dimensionality, an extra weight matrix W is trained to condense the different attention heads into a matrix with the same size as one Z matrix. This way, the amount of data given to the next step does not enlarge every time self-attention is performed.

When performing self-attention, information about the order of the different elements within the sequence is lost. To address this problem, positional encodings are added to the embedding vectors. Every position has its unique positional encoding vector. These vectors follow a specific pattern, which the Transformer model can learn to recognize. This way, the model can consider distances between the different elements.

As discussed above, in the core of self-attention are three objects: queries (Q), keys (K), and values (V). Each of these objects has an inner semantic meaning of their purpose. One can think of these as analogous to databases. We have a user-defined query of what the user wants to know. Then we have the relations in the database, i.e., the values which are the weights. More advanced database management systems create some apt representation of its relations to retrieve values more efficiently from the relations. This can be achieved by using indexes, which represent information about what is stored in the database. In the context of attention, indexes can be thought of as keys. So instead of running the query against values directly, the query is first executed on the indexes to retrieve where the relevant values or weights are stored. Lastly, these weights are run against the original values to retrieve data that is most relevant to the initial query.

Figure 16:
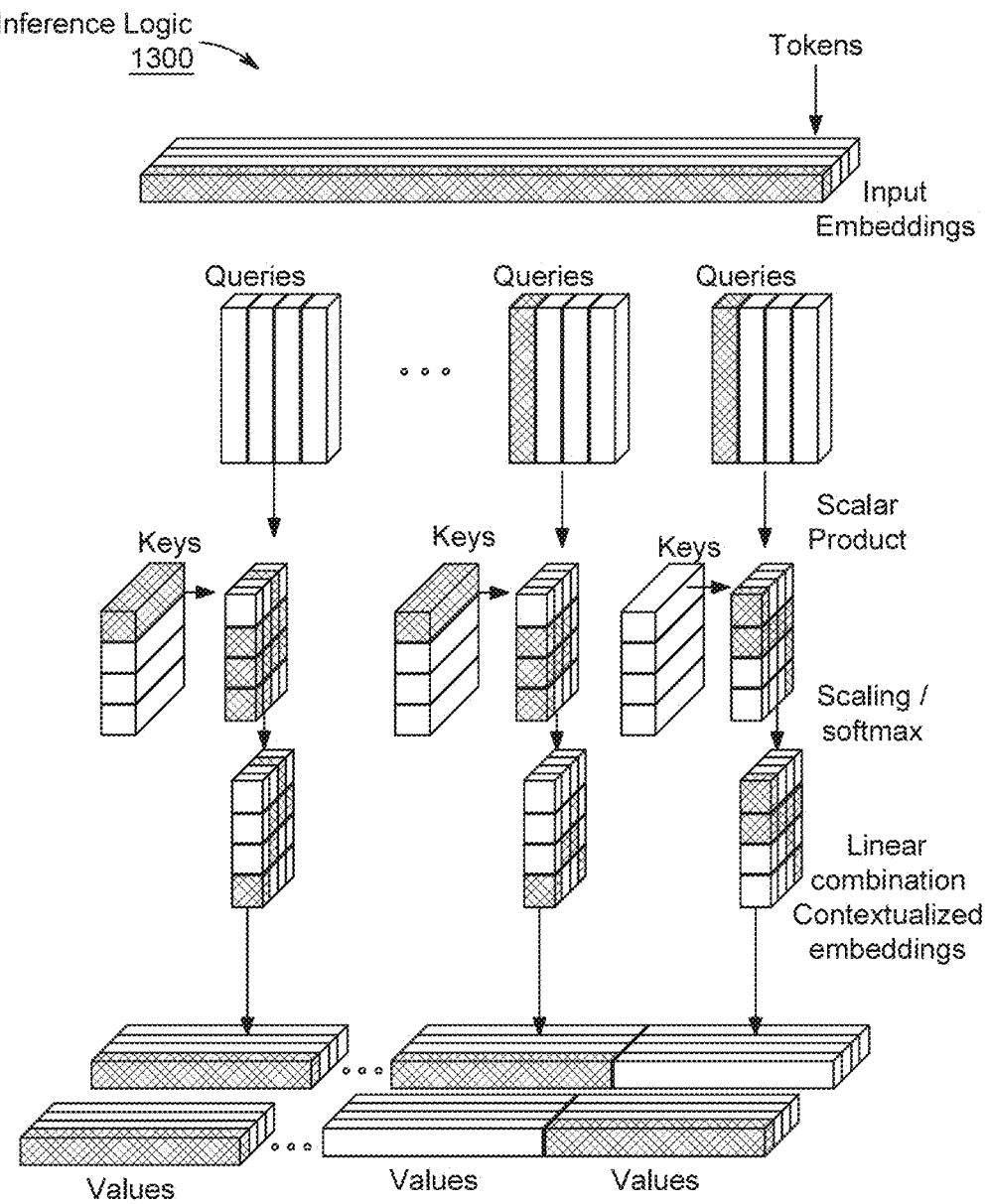
FIG. 16 is a depiction of several attention heads in a Transformer block.

FIG. 16 depicts several attention heads in a Transformer block. We can see that the outputs of queries and keys dot products in different attention heads are differently colored. This depicts the capability of the multi-head attention to focus on different aspects of the input and aggregate the obtained information by multiplying the input with different attention weights.

Examples of attention calculation include scaled dot-product attention and additive attention. There are several reasons why scaled dot-product attention is used in the Transformers. Firstly, the scaled dot-product attention is relatively fast to compute, since its main parts are matrix operations that can be run on modern hardware accelerators. Secondly, it performs similarly well for smaller dimensions of the K matrix, dk, as the additive attention. For larger dk, the scaled dot-product attention performs a bit worse because dot products can cause the vanishing gradient problem. This is compensated via the scaling factor, which is defined as $\sqrt{dk}$.

As discussed above, the attention function takes as input three objects: key, value, and query. In the context of Transformers, these objects are matrices of shapes (n, d), where n is the number of elements in the input sequence and d is the hidden representation of each element (also called the hidden vector). Attention is then computed as:

Attention (Q, K, V)=SoftMax $$\left(\frac{QK^T}{\sqrt{dk}}\right) V$$

where Q, K, V are computed as:

$X \cdot W_Q$, $X \cdot W_K$, $X \cdot W_V$

X is the input matrix and $W_Q$, $W_K$, $W_V$ are learned weights to project the input matrix into the representations. The dot products appearing in the attention function are exploited for their geometrical interpretation where higher values of their results mean that the inputs are more similar, i.e., pointing in the geometrical space in the same direction. Since the attention function now works with matrices, the dot product becomes matrix multiplication. The SoftMax function is used to normalize the attention weights into the value of 1 prior to being multiplied by the values matrix. The resulting matrix is used either as input into another layer of attention or becomes the output of the Transformer.

Multi-Head Attention

Transformers become even more powerful when multi-head attention is used. Queries, keys, and values are computed the same way as above, though they are now projected into h different representations of smaller dimensions using a set of h learned weights. Each representation is passed into a different scaled dot-product attention block called a head. The head then computes its output using the same procedure as described above.

Formally, the multi-head attention is defined as:

MultiHeadAttention (Q, K, V)=[head$_1$, . . . , head$_h$]W$_0$ where head$_i$=Attention (QW$_i^Q$, KW$_i^K$, VW$_i^V$)

The outputs of all heads are concatenated together and projected again using the learned weights matrix W$_0$ to match the dimensions expected by the next block of heads or the output of the Transformer. Using the multi-head attention instead of the simpler scaled dot-product attention enables Transformers to jointly attend to information from different representation subspaces at different positions.

Figure 17:
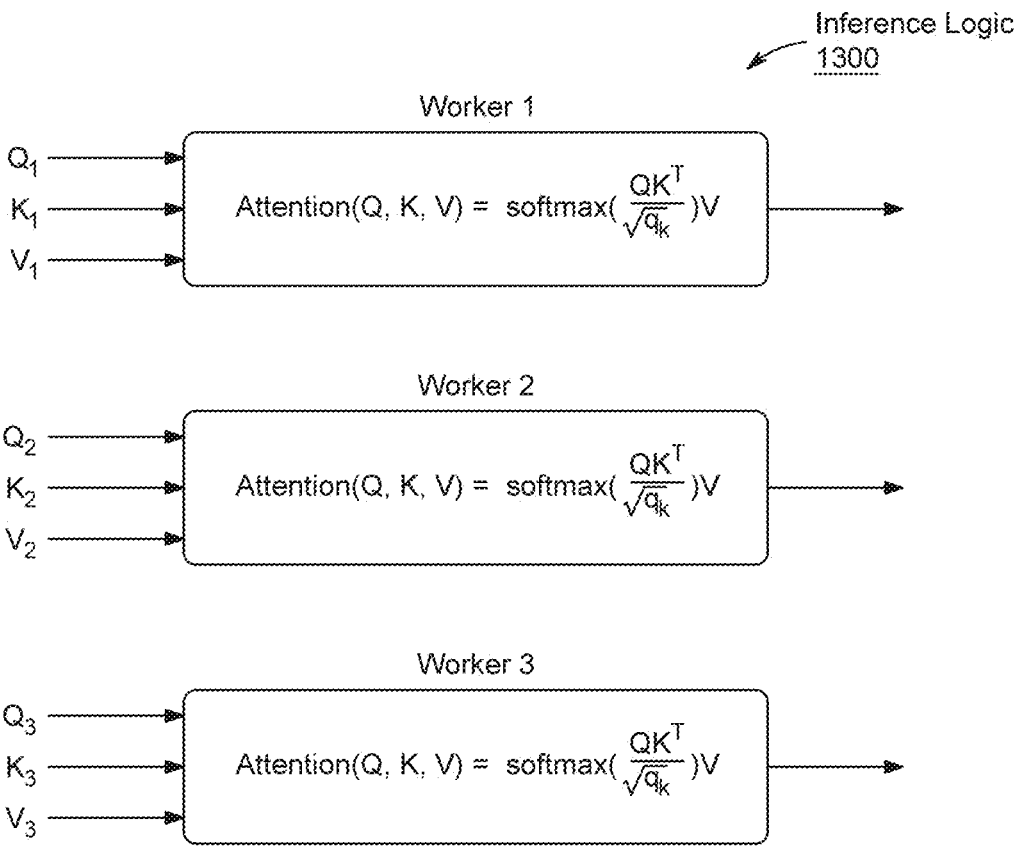
FIG. 17 is an illustration that shows how one can use multiple workers to compute the multi-head attention in parallel, as the respective heads compute their outputs independently of one another.

As shown in FIG. 17, one can use multiple workers to compute the multi-head attention in parallel, as the respective heads compute their outputs independently of one another. Parallel processing is one of the advantages of Transformers over RNNs.

Assuming the naive matrix multiplication algorithm which has a complexity of:

$a \cdot b \cdot c$

For matrices of shape (a, b) and (c, d), to obtain values Q, K, V, we need to compute the operations:

$X \cdot W_Q$, $X \cdot W_K$, $X \cdot W_V$

The matrix X is of shape (n, d) where n is the number of patches and d is the hidden vector dimension. The weights $W_Q$, $W_K$, $W_V$ are all of shape (d, d). Omitting the constant factor 3, the resulting complexity is:

$n \cdot d^2$

We can proceed to the estimation of the complexity of the attention function itself, i.e., of SoftMax $$\left(\frac{QK^T}{\sqrt{dk}}\right) V.$$

The matrices Q and K are both of shape (n, d). The transposition operation does not influence the asymptotic complexity of computing the dot product of matrices of shapes (n, d)·(d, n), therefore its complexity is:

$n^2 \cdot d$

Scaling by a constant factor of d, where dk is the dimension of the keys vector, as well as applying the SoftMax function, both have the complexity of a·b for a matrix of shape (a, b), hence they do not influence the asymptotic complexity. Lastly the dot product SoftMax $$\left(\frac{QK^T}{\sqrt{dk}}\right) \cdot V$$

is between matrices of shapes (n, n) and (n, d) and so its complexity is:

$$n^2 \cdot d$$

The final asymptotic complexity of scaled dot-product attention is obtained by summing the complexities of computing Q, K, V, and of the following attention function:

$$n \cdot d^2 + n^2 \cdot d.$$

The asymptotic complexity of multi-head attention is the same since the original input matrix X is projected into h matrices of shapes (n, d/h), where h is the number of heads. From the point of view of asymptotic complexity, h is constant, therefore we would arrive at the same estimate of asymptotic complexity using a similar approach as for the scaled dot-product attention.

Transformer models often have the encoder-decoder architecture, although this is not necessarily the case. The encoder is built out of different encoder layers which are all constructed in the same way. The positional encodings are added to the embedding vectors. Afterward, self-attention is performed.

Encoder Block of Transformer

Figure 18:
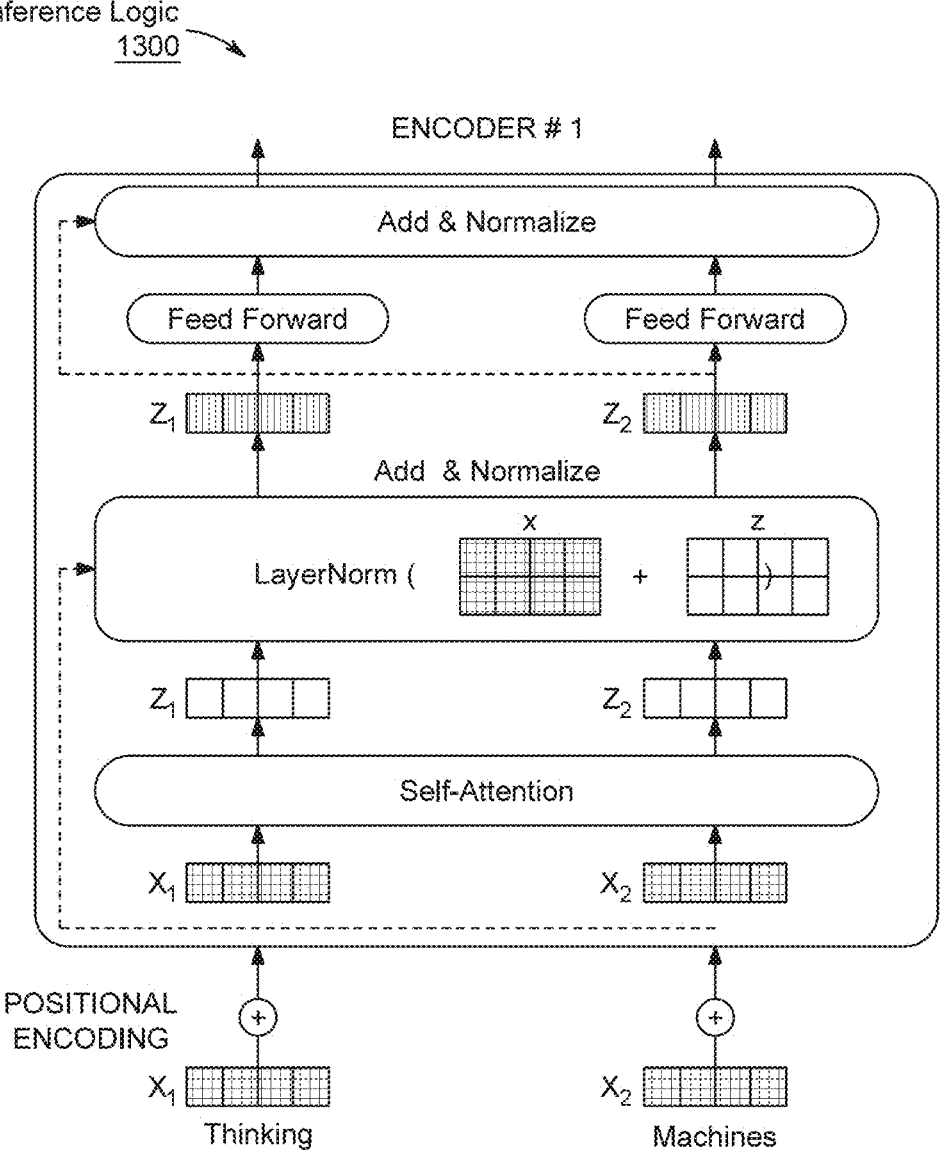
FIG. 18 is a portrayal of one encoder layer of a Transformer network.

FIG. 18 portrays one encoder layer of a Transformer network. Every self-attention layer is surrounded by a residual connection, summing up the output and input of the self-attention. This sum is normalized, and the normalized vectors are fed to a feed-forward layer. Every z vector is fed separately to this feed-forward layer. The feed-forward layer is wrapped in a residual connection and the outcome is normalized too. Often, numerous encoder layers are piled to form the encoder. The output of the encoder is a fixed-size vector for every element of the input sequence.

Just like the encoder, the decoder is built from different decoder layers. In the decoder, a modified version of self-attention takes place. The query vector is only compared to the keys of previous output sequence elements. The elements further in the sequence are not known yet, as they still must be predicted. No information about these output elements may be used.

Encoder-Decoder Blocks of Transformer

Figure 19:
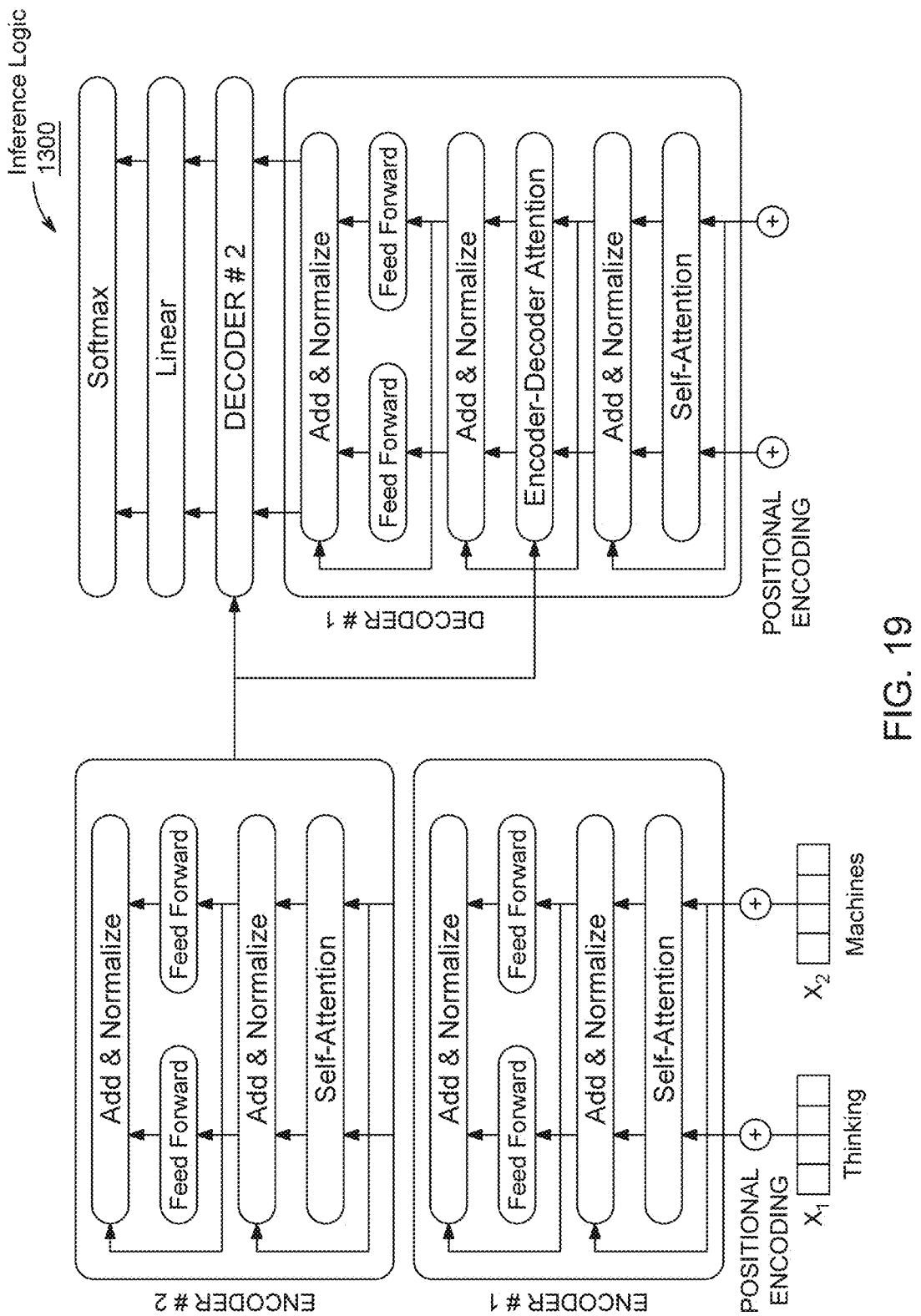
FIG. 19 shows a schematic overview of a Transformer model.
Figures 20A, 20B:
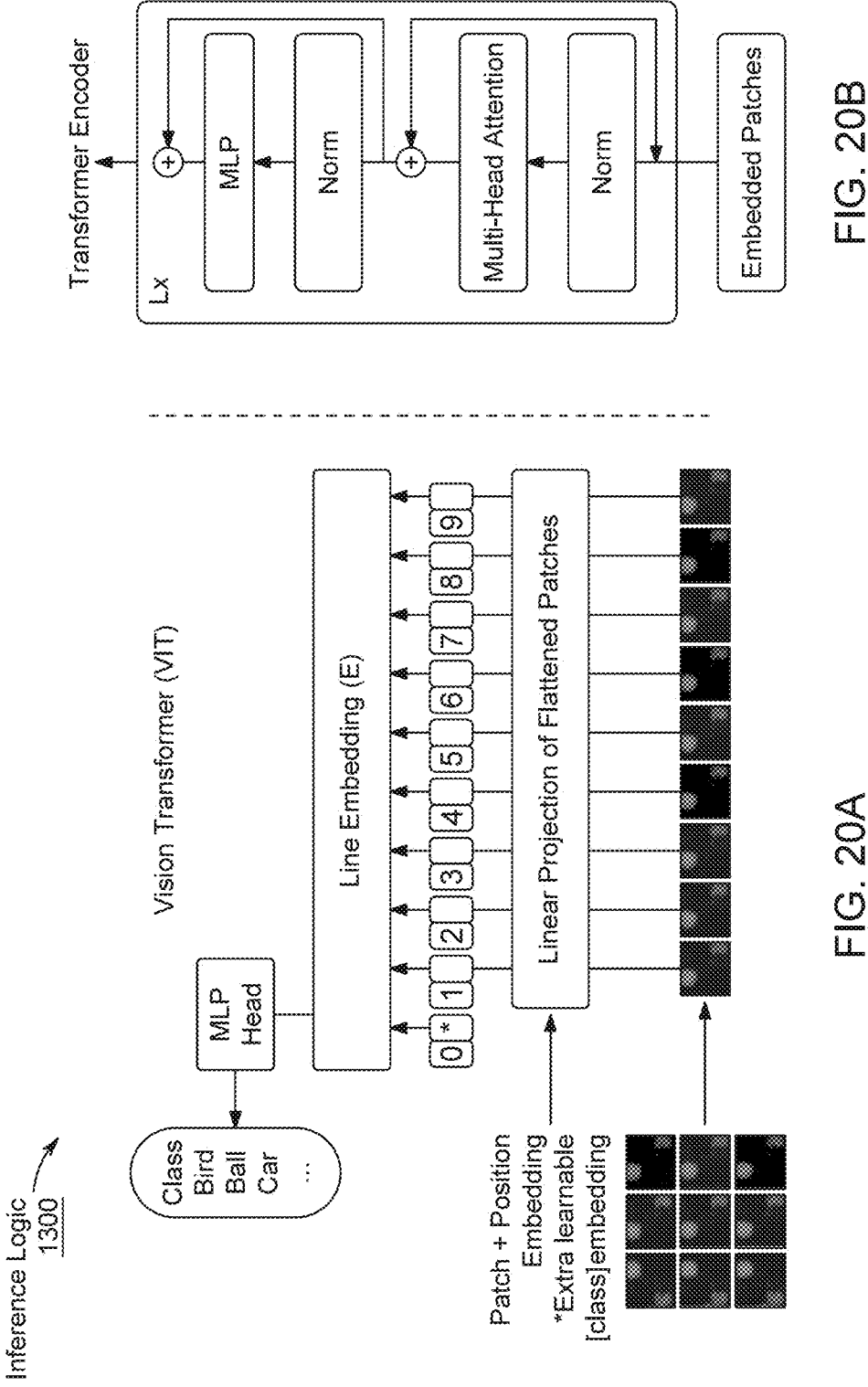
FIGS. 20A and 20B is a depiction of a Vision Transformer (ViT).
Figures 21A, 21B, 21C, 21D:
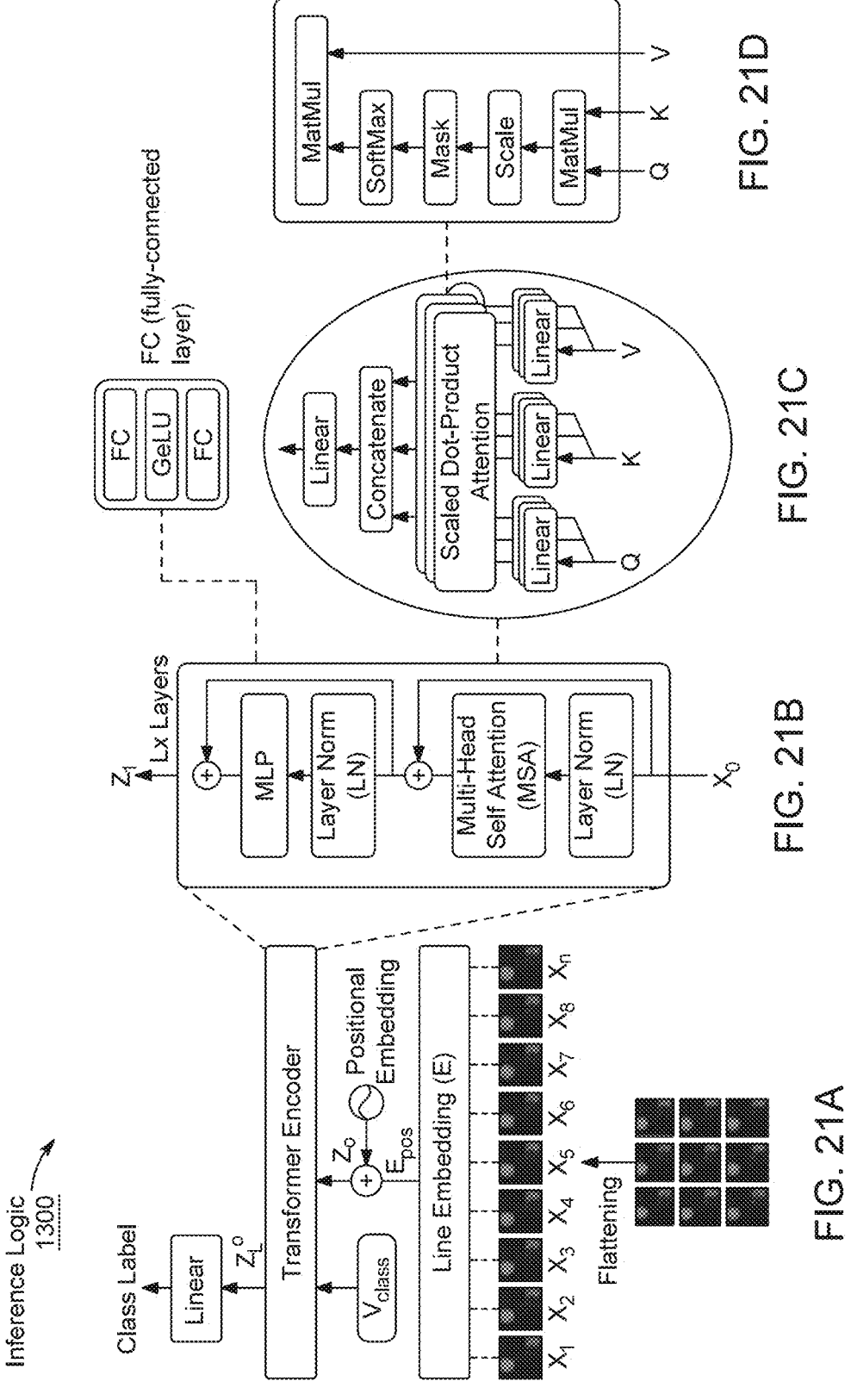
FIG. 21A-D illustrates a processing flow of the Vision Transformer (ViT).

FIG. 19 shows a schematic overview of a Transformer model. Next to a self-attention layer, a layer of encoder-decoder attention is present in the decoder, in which the decoder can examine the last Z vectors of the encoder, providing fluent information transmission. The ultimate decoder layer is a feed-forward layer. All layers are packed in a residual connection. This allows the decoder to examine all previously predicted outputs and all encoded input vectors to predict the next output. Thus, information from the encoder is provided to the decoder, which could improve the predictive capacity. The output vectors of the last decoder layer need to be processed to form the output of the entire system. This is done by a combination of a feed-forward layer and a SoftMax function. The output corresponding to the highest probability is the predicted output value for a subject time step.

For some tasks other than translation, only an encoder is needed. This is true for both document classification and name entity recognition. In these cases, the encoded input vectors are the input of the feed-forward layer and the SoftMax layer. Transformer models have been extensively applied in different NLP fields, such as translation, document summarization, speech recognition, and named entity recognition. These models have applications in the field of biology as well for predicting protein structure and function and labeling DNA sequences.

Vision Transformer

There are extensive applications of transformers in vision including popular recognition tasks (e.g., image classification, object detection, action recognition, and segmentation), generative modeling, multi-modal tasks (e.g., visual-question answering, visual reasoning, and visual grounding), video processing (e.g., activity recognition, video forecasting), low-level vision (e.g., image super-resolution, image enhancement, and colorization) and 3D analysis (e.g., point cloud classification and segmentation).

Transformers were originally developed for NLP and worked with sequences of words. In image classification, we often have a single input image in which the pixels are in a sequence. To reduce the computation required, Vision Transformers (ViTs) cut the input image into a set of fixed-sized patches of pixels. The patches are often 16×16 pixels. They are treated much like words in NLP Transformers. ViTs are depicted in FIGS. 20A, 20B, 21A, 21B, 21C, and 21D. Unfortunately, important positional information is lost because image sets are position-invariant. This problem is solved by adding a learned positional encoding into the image patches.

The computations of the ViT architecture can be summarized as follows. The first layer of a ViT extracts a fixed number of patches from an input image (20A). The patches are then projected to linear embeddings. A special class token vector is added to the sequence of embedding vectors to include all representative information of all tokens through the multi-layer encoding procedure. The class vector is unique to each image. Vectors containing positional information are combined with the embeddings and the class token. The sequence of embedding vectors is passed into the Transformer blocks. The class token vector is extracted from the output of the last Transformer block and is passed into a multilayer perceptron (MLP) head whose output is the final classification. The perceptron takes the normalized input and places the output in categories. It classifies the images. This procedure directly translates into the Python Keras code shown in FIG. 22.

When the input image is split into patches, a fixed patch size is specified before instantiating a ViT. Given the quadratic complexity of attention, patch size has a large effect on the length of training and inference time. A single Transformer block comprises several layers. The first layer implements Layer Normalization, followed by the multi-head attention that is responsible for the performance of ViTs. In the depiction of a Transformer block in FIG. 20B, we can see two arrows. These are residual skip connections. Including skip connection data can simplify the output and improve the results. The output of the multi-head attention is followed again by Layer Normalization. And finally, the output layer is an MLP (Multi-Layer Perceptron) with the GELU (Gaussian Error Linear Unit) activation function.

ViTs can be pretrained and fine-tuned. Pretraining is generally done on a large dataset. Fine-tuning is done on a domain specific dataset.

Domain-specific architectures, like convolutional neural networks (CNNs) or long short-term memory networks (LSTMs), have been derived from the usual architecture of MLPs and suffer from so-called inductive biases that predispose the networks towards a certain output. ViTs stepped in the opposite direction of CNNs and LSTMs and became more general architectures by eliminating inductive biases. A ViT can be seen as a generalization of MLPs because MLPs, after being trained, do not change their weights for different inputs. On the other hand, ViTs compute their attention weights at runtime based on the particular input.

The following detailed description is made with reference to the figures. Example implementations are described to illustrate the technology disclosed, not to limit its scope, which is defined by the claims. Those of ordinary skill in the art will recognize a variety of equivalent variations on the description that follows. Reference will now be made in detail to the exemplary implementations of the present disclosure, examples of which are illustrated in the accompanying drawings. Wherever possible, the same reference numbers will be used throughout the drawings to refer to the same or like parts.

The following discussion is presented to enable any person skilled in the art to make and use the technology disclosed and is provided in the context of a particular application and its requirements. Various modifications to the disclosed implementations will be readily apparent to those skilled in the art, and the general principles defined herein may be applied to other implementations and applications without departing from the spirit and scope of the technology disclosed. Thus, the technology disclosed is not intended to be limited to the implementations shown but is to be accorded the widest scope consistent with the principles and features disclosed herein.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

The detailed description of various implementations will be better understood when read in conjunction with the appended drawings. To the extent that the figures illustrate diagrams of the functional blocks of the various implementations, the functional blocks are not necessarily indicative of the division between hardware circuitry. Thus, for example, one or more of the functional blocks (e.g., modules, processors, or memories) may be implemented in a single piece of hardware (e.g., a general-purpose signal processor or a block of random-access memory, hard disk, or the like) or multiple pieces of hardware. Similarly, the programs may be stand-alone programs, may be incorporated as subroutines in an operating system, may be functions in an installed software package, and the like. It should be understood that the various implementations are not limited to the arrangements and instrumentality shown in the drawings.

The processing engines and databases of the figures, designated as modules, can be implemented in hardware or software, and need not be divided up in precisely the same blocks as shown in the figures. Some of the modules can also be implemented on different processors, computers, or servers, or spread among a number of different processors, computers, or servers. In addition, it will be appreciated that some of the modules can be combined, operated in parallel or in a different sequence than that shown in the figures without affecting the functions achieved. The modules in the figures can also be thought of as flowchart steps in a method. A module also need not necessarily have all its code disposed contiguously in memory; some parts of the code can be separated from other parts of the code with code from other modules or other functions disposed in between.

Computer Architecture

Figure 23:
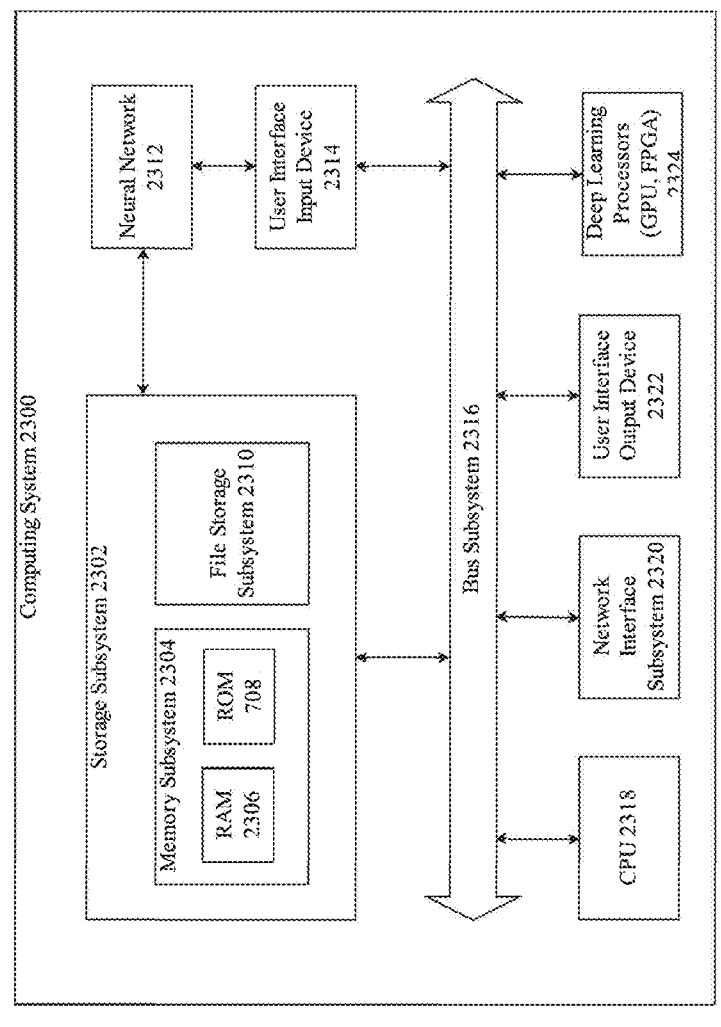
FIG. 23 shows an example computer system that can be used to implement the technology disclosed, according to certain embodiments.

FIG. 23 shows an example computer system 2300 that can be used to implement the technology disclosed. The computer system 2300 is a representation of the system 100, as described in FIG. 1B. The computer system 2300 includes at least one central processing unit (CPU) 2318 that communicates with a number of peripheral devices via bus subsystem 2316. These peripheral devices can include a storage subsystem 2302 including, for example, memory devices and a file storage subsystem 2310, user interface input devices 2314, user interface output devices 2322, and a network interface subsystem 2320. The input and output devices allow user interaction with computer system 2300. Network interface subsystem 2320 provides an interface to outside networks, including an interface to corresponding interface devices in other computer systems.

In one implementation, a neural network 2312 is communicably linked to the storage subsystem 2302 and the user interface input devices 2314.

User interface input devices 2314 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system 2300.

User interface output devices 2322 can include a display subsystem, a printer, a fax machine, or non-visual displays such as audio output devices. The display subsystem can include an LED display, a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system 2300 to the user or to another machine or computer system.

Storage subsystem 2302 stores programming and data constructs that provide the functionality of some or all of the modules and methods described herein. These software modules are generally executed by deep learning processors 2324.

Deep learning processors 2324 can be graphics processing units (GPUs), field-programmable gate arrays (FPGAs), application-specific integrated circuits (ASICs), and/or coarse-grained reconfigurable architectures (CGRAs). Processors 2324 can be hosted by a deep learning cloud platform such as Google Cloud Platform™, Xilinx™, and Cirrascale™ Examples of processors 2324 include Google's Tensor Processing Unit (TPU)™, rackmount solutions like GX4 Rackmount Series™, GX6 Rackmount Series™, NVIDIA DGX-1™ Microsoft's Stratix V FPGA™, Graphcore's Intelligent Processor Unit (IPU)™, Qualcomm's Zeroth Platform™ with Snapdragon Processors™, NVIDIA's Volta™, NVIDIA's DRIVE PX™, NVIDIA's JETSON TX1/TX2 MODULE™, Intel's Nirvana™, Movidius VPU™ Fujitsu DPI™, ARM's DynamicIQ™, IBM TrueNorth™, Lambda GPU Server with Testa V100s™, and others.

Memory subsystem 2304 used in the storage subsystem 2302 can include a number of memories including a main random-access memory (RAM) 2306 for storage of instructions and data during program execution and a read only memory (ROM) 2308 in which fixed instructions are stored. A file storage subsystem 2310 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem 2310 in the storage subsystem 2302, or in other machines accessible by the processor.

Bus subsystem 2316 provides a mechanism for letting the various components and subsystems of computer system 2300 communicate with each other as intended. Although bus subsystem 2316 is shown schematically as a single bus, alternative implementations of the bus subsystem can use multiple buses.

Computer system 2300 itself can be of varying types including a personal computer, a portable computer, a workstation, a computer terminal, a network computer, a television, a mainframe, a server farm, a widely distributed set of loosely networked computers, or any other data processing system or user device. Due to the ever-changing nature of computers and networks, the description of computer system 2300 depicted in FIG. 23 is intended only as a specific example for the purpose of illustrating the preferred implementations of the present technology disclosed. Many other configurations of computer system 2300 are possible having more or fewer components than the computer system depicted in FIG. 23.

In various implementations, a learning system is provided. In some implementations, a feature vector is provided to a learning system. Based on the input features, the learning system generates one or more outputs. In some implementations, the output of the learning system is a feature vector. In some implementations, the learning system comprises an SVM. In other implementations, the learning system comprises an artificial neural network. In some implementations, the learning system is pre-trained using training data. In some implementations training data is retrospective data. In some implementations, the retrospective data is stored in a data store. In some implementations, the learning system may be additionally trained through manual curation of previously generated outputs.

In some implementations, an object detection pipeline is a trained classifier. In some implementations, the trained classifier is a random decision forest. However, it will be appreciated that a variety of other classifiers are suitable for use according to the present disclosure, including linear classifiers, support vector machines (SVM), or neural networks such as recurrent neural networks (RNN).

Suitable artificial neural networks include but are not limited to a feedforward neural network, a radial basis function network, a self-organizing map, learning vector quantization, a recurrent neural network, a Hopfield network, a Boltzmann machine, an echo state network, long short term memory, a bi-directional recurrent neural network, a hierarchical recurrent neural network, a stochastic neural network, a modular neural network, an associative neural network, a deep neural network, a deep belief network, a convolutional neural networks, a convolutional deep belief network, a large memory storage and retrieval neural network, a deep Boltzmann machine, a deep stacking network, a tensor deep stacking network, a spike and slab restricted Boltzmann machine, a compound hierarchical-deep model, a deep coding network, a multilayer kernel machine, or a deep Q-network.

The present disclosure may be embodied as a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer system/server may be described in the general context of computer system-executable instructions, such as program modules, being executed by a computer system. Generally, program modules may include routines, programs, objects, components, logic, data structures, and so on that perform particular tasks or implement particular abstract data types. Computer system/server may be practiced in distributed computing environments where tasks are performed by remote processing devices that are linked through a communications network. In a distributed computing environment, program modules may be located in both local and remote computer system storage media including memory storage devices.

As shown in FIG. 23, computer system/server in computing node is shown in the form of a general-purpose computing device. The components of computer system/server may include, but are not limited to, one or more processors or processing units, a system memory, and a bus that couples various system components including system memory to processor.

The bus represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, Peripheral Component Interconnect (PCI) bus, Peripheral Component Interconnect Express (PCIe), and Advanced Microcontroller Bus Architecture (AMBA).

Computer system/server typically includes a variety of computer system readable media. Such media may be any available media that is accessible by computer system/server, and it includes both volatile and non-volatile media, removable and non-removable media.

System memory can include computer system readable media in the form of volatile memory, such as random access memory (RAM) and/or cache memory. Algorithm Computer system/server may further include other removable/non-removable, volatile/non-volatile computer system storage media. By way of example only, storage system can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus by one or more data media interfaces. As will be further depicted and described below, memory may include at least one program product having a set (e.g., at least one) of program modules that are configured to carry out the functions of embodiments of the disclosure.

Clauses

The technology disclosed can be practiced as a system, method, or article of manufacture. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

One or more implementations and clauses of the technology disclosed, or elements thereof can be implemented in the form of a computer product, including a non-transitory computer readable storage medium with computer usable program code for performing the method steps indicated. Furthermore, one or more implementations and clauses of the technology disclosed, or elements thereof can be implemented in the form of an apparatus including a memory and at least one processor that is coupled to the memory and operative to perform exemplary method steps. Yet further, in another aspect, one or more implementations and clauses of the technology disclosed or elements thereof can be implemented in the form of means for carrying out one or more of the method steps described herein; the means can include (i) hardware module(s), (ii) software module(s) executing on one or more hardware processors, or (iii) a combination of hardware and software modules; any of (i)-(iii) implement the specific techniques set forth herein, and the software modules are stored in a computer readable storage medium (or multiple such media).

The clauses described in this section can be combined as features. In the interest of conciseness, the combinations of features are not individually enumerated and are not repeated with each base set of features. The reader will understand how features identified in the clauses described in this section can readily be combined with sets of base features identified as implementations in other sections of this application. These clauses are not meant to be mutually exclusive, exhaustive, or restrictive; and the technology disclosed is not limited to these clauses but rather encompasses all possible combinations, modifications, and variations within the scope of the claimed technology and its equivalents.

Other implementations of the clauses described in this section can include a non-transitory computer readable storage medium storing instructions executable by a processor to perform any of the clauses described in this section. Yet another implementation of the clauses described in this section can include a system including memory and one or more processors operable to execute instructions, stored in the memory, to perform any of the clauses described in this section.

Clauses

1. The system further comprising a hands-free interaction module providing voice commands, gesture recognition, gaze selection, and haptic input, the processing circuitry being configured to accept a user action to confirm a candidate access site, adjust overlay parameters, or change a capture configuration.

2. In the system, the processing circuitry comprises models for segmentation and adaptive overlay stabilization that compensate for patient and provider motion.

3. In the system, the processing circuitry is configured to update model parameters by a federated learning module using site-local training signals without transmitting raw patient imaging data outside a deployment site.

4. In the system, the processing circuitry executes on on-device compute within a wearable unit and is further in communication with at least one of an edge node and a cloud service, and is configured to operate in an offline fallback mode and synchronize procedure metadata when connectivity is restored.

5. The system further comprising an interface to clinical systems, the processing circuitry being configured to log a procedure record including the candidate access site, the trajectory, the imaging system used, and presentation parameters, and to store or retrieve patient data in an electronic health record.

The invention claimed is:

1. A system, comprising:

an imaging system configured to acquire imaging data of tissue structure and anatomical structures of a patient;

a processing circuitry comprising at least one processor and memory storing instructions that, when executed by the at least one processor, cause the processing circuitry to:

segment anatomical structures in the imaging data;

estimate a target depth and a target dimension for a target anatomical structure;

compute a candidate access site and a trajectory comprising at least one of an insertion path and an incision path based on the segmentation and the estimated target depth and the estimated target dimension; and maintain adaptive overlay alignment by using a patient coordinate frame and a display coordinate frame, wherein the alignment is continuously updated to compensate for patient motion and device motion; and an extended-reality device, comprising a head-worn display and a projection module, configured to present patient-registered overlays through the head-worn display and to project the overlays onto patient skin using an adaptive calibration.

2. The system of claim 1, wherein the imaging system comprises a plurality of imaging modalities including ultrasound, infrared, near-infrared, photoacoustic imaging, optical coherence tomography, transillumination, hyperspectral imaging, and laser speckle contrast imaging.

3. The system of claim 1, wherein the processing circuitry constrains the trajectory to satisfy at least one constraint comprising a minimum target-dimension threshold and a maximum target-depth threshold, and wherein, for vascular targets, an around an identified artery are loaded from an institution-approved policy profile and logged with a procedure record.

4. The system of claim 1, wherein the processing circuitry computes a predictive indicator of procedural success for the candidate access site using historical outcome data and encodes the predictive indicator within the overlays.

5. The system of claim 1, wherein the projection module projects the overlays onto patient skin using a projection calibration derived from a three-dimensional patient surface model, and wherein the processing circuitry updates the projection calibration responsive to motion.

6. The system of claim 1, wherein a step of registration that maintains adaptive overlay alignment between the patient coordinate frame and the display coordinate frame is based on sensor fusion of signals from at least two sensor types selected from depth sensing, structured light, LiDAR, inertial measurement, and acoustic or ultrasound beacons.

7. The system of claim 1, further comprising a telemedicine interface, the processing circuitry being configured to receive remote annotations and render the remote annotations within the patient-registered overlays in real time.

8. The system of claim 1, further comprising an observer-view output configured to present, to an external display, a synchronized view of the patient-registered overlays and to accept a remote expert input that is incorporated into the overlays.

9. The system of claim 1, further comprising an extended-reality rendering subsystem configurable to present mixed-reality synthetic three-dimensional reconstructions of the anatomical structures.

10. The system of claim 1, wherein the imaging system further comprises computed tomography, magnetic resonance imaging, and X-ray or fluoroscopic imaging.

11. The system of claim 1, wherein the processing circuitry is configured to retrieve historical imaging data from a picture-archiving and communication system or an electronic health record and to register the historical imaging data with real-time imaging for longitudinal visualization.

12. The system of claim 1, wherein the processing circuitry references prior procedural records to identify previously used or contraindicated access locations within a configurable temporal window and automatically suppresses candidate access sites or trajectories in identified regions.

13. The system of claim 1, wherein the extended-reality device or an associated camera captures an image of an insertion or incision site, associates the image with spatial coordinates, timestamps, and operator identifiers, and uploads an annotated record to an electronic health record.

14. The system of claim 1, wherein model-based segmentation utilizes prior imaging volumes as anatomical priors or patient-specific digital-twin references to improve overlay stability and predictive accuracy during repeat procedures.

15. The system of claim 1, wherein a projection calibration is derived from a three-dimensional surface model of patient skin and is automatically refreshed when an alignment confidence metric falls below a threshold.

16. The system of claim 1, wherein overlay presentation is inhibited or a recalibration prompt is projected when an alignment confidence metric drops below a preset value.

17. The system of claim 1, wherein the target anatomical structure comprises a cardiac structure and the processing circuitry is configured to register historical cardiac imaging with live echocardiography, to recommend transducer positions and orientations, and to present overlays of transducer guidance and live ultrasound findings on the head-worn display or an external display.

18. The system of claim 1, wherein the extended-reality device is operable in a clinician-selectable overlay-only mode in which the processing circuitry presents patient-registered overlays while suppressing automated recommendations for the candidate access site and the trajectory.

19. The system of claim 1, further configured to record and store data corresponding to each insertion or incision event, a spatial location, a trajectory, a depth, a timestamp, and an operator identifier, to define an exclusion region within a configurable spatial neighborhood and a configurable temporal window of the recorded event, and to suppress or deprioritize candidate access sites or trajectories whose spatial locations fall within the exclusion region so as to avoid repeated puncture of the same anatomical region within a short time proximity.

20. A computer-implemented method comprising:

acquiring imaging data of tissue structure and anatomical structures of a patient;

segmenting anatomical structures in the imaging data;

estimating a target depth and a target dimension for a target anatomical structure;

computing a candidate access site and a trajectory comprising at least one of an insertion path and an incision path based on the segmentation and the estimated target depth and the estimated target dimension;

maintaining adaptive overlay alignment by using a patient coordinate frame and a display coordinate frame, wherein the alignment is continuously updated to compensate for patient motion and device motion; and presenting patient-registered overlays through a head-worn display and projecting the overlays onto patient skin using an adaptive calibration.

* * * * *